(12) United States Patent
Okamoto et al.

(10) Patent No.: US 8,716,513 B2
(45) Date of Patent: May 6, 2014

(54) PROCESS FOR PRODUCTION OF BIS-QUATERNARY AMMONIUM SALT, AND NOVEL INTERMEDIATE

(75) Inventors: Kuniaki Okamoto, Kawagoe (JP); Tsutomu Watahiki, Kawagoe (JP); Motoshige Sumino, Kawagoe (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 32 days.

(21) Appl. No.: 13/387,887

(22) PCT Filed: Aug. 5, 2010

(86) PCT No.: PCT/JP2010/063301
§ 371 (c)(1),
(2), (4) Date: Jan. 30, 2012

(87) PCT Pub. No.: WO2011/016523
PCT Pub. Date: Feb. 10, 2011

(65) Prior Publication Data
US 2012/0130107 A1 May 24, 2012

(30) Foreign Application Priority Data
Aug. 7, 2009 (JP) ................. 2009-184641

(51) Int. Cl.
*C07C 309/73* (2006.01)
*C07C 303/32* (2006.01)

(52) U.S. Cl.
USPC ............................................ 558/46; 562/101

(58) Field of Classification Search
USPC ............................................ 558/46; 562/101
See application file for complete search history.

(56) References Cited

U.S. PATENT DOCUMENTS

| 4,163,005 | A | 7/1979 | Albright |
| 5,382,496 | A | 1/1995 | Sakai et al. |
| 2002/0061832 | A1 | 5/2002 | Reinehr et al. |
| 2009/0035693 | A1 | 2/2009 | Sato et al. |
| 2010/0041916 | A1 | 2/2010 | Okamoto et al. |
| 2011/0130305 | A1 * | 6/2011 | Patton et al. .......... 506/15 |

FOREIGN PATENT DOCUMENTS

| EP | 0825175 | 2/1998 |
| EP | 1191016 | 3/2002 |
| EP | 2067770 | 6/2009 |
| JP | 54-36232 | 3/1979 |
| JP | 3-83963 | 4/1991 |
| JP | 6-242534 | 9/1994 |
| JP | 9-77610 | 3/1997 |
| JP | 9-132504 | 5/1997 |
| JP | 10-114604 | 5/1998 |
| JP | 2000-178104 | 6/2000 |
| JP | 2002-55407 | 2/2002 |
| JP | 2002-187874 | 7/2002 |
| JP | 2004-217501 | 8/2004 |
| JP | 2005-511666 | 4/2005 |
| JP | 2008-1638 | 1/2008 |
| JP | 2009-36863 | 2/2009 |
| WO | 03/048078 | 6/2003 |
| WO | WO 2005/030782 | 4/2005 |
| WO | 2008/032463 | 3/2008 |

OTHER PUBLICATIONS

D.J. Chadbourne and A.J. Nunn, "Some Alkyl and Substituted Alkyl 2,4-Dinitrobenzene-sulphonates and Polymethylene Bis-2,4-dinitrobenzenesulphonates," Journal of the Chemical Society (1965), p. 4458-4463.

(Continued)

*Primary Examiner* — Kristin Vajda
(74) *Attorney, Agent, or Firm* — Hamre, Schumann, Mueller & Larson, P.C.

(57) ABSTRACT

Object To provide a method for producing a bis-quaternary ammonium salt efficiently and a novel synthetic intermediate thereof.

Solution The present invention relates to a method for producing a bis-quaternary ammonium salt represented by a general formula [3] which comprises reacting a disulfonic acid ester represented by a general formula [1] (in the formula, definitions of two $R^1$'s and T are as described in claim 1) with a tertiary amine represented by a general formula [2] (in the formula, definitions of $R^3$ to $R^5$ are as described in claim 1), and a disulfonic acid ester represented by a general formula [1'] (in the formula, two $R^{16}$'s represent independently a halogen atom or a C1-C3 fluoroalkyl group, and two m's represent independently an integer of 1 to 5).

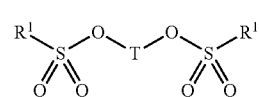

[1]

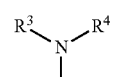

[2]

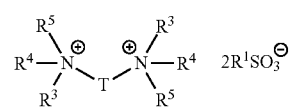

[3]

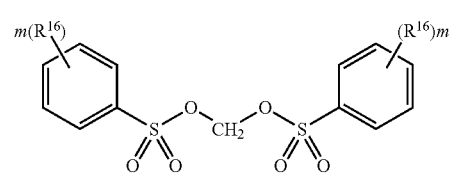

[1']

5 Claims, 1 Drawing Sheet

(56) References Cited

OTHER PUBLICATIONS

I.L. Mushkalo and L.S. Turova, "3,3'-Ethylenebis (benzothiazolium) salts and their biscyanine dyes," Ukrainskii Khimicheskii Zhurnal (1977), vol. 43, No. 9, p. 953-956.
Nishizeki et al.: "Preparation of bis [(arylsulfonoxy) methyl] ethers as intermediates for methyl ether photographic materials"; Database CA [online] Chemical Abstract Service, Columbus, Ohio, US; 1991, XP002690762 (JP 3-083963, Apr. 9, 1991), 14 pages.

Mushkalo et al.: "3,3'-Ethylenebis (benzothiazolium) salts and their biscyanine dyes"; Database CA [online] Chemical Abstracts Service, Columbus, Ohio, US; 1978, XP002690763, 1 page.
Chadbourne et al.: "Some Alkyl and Substituted Alkyl 2,4-Dinitrobenzenesulphonates and Polymethylene Bis-2,4-dinitrobenzenesulphonates"; Journal of the Chemical Society, Chemical Society, Letchworth; GB, Jan. 1, 1965, pp. 4458-4463, XP008149764, 6 pages.

\* cited by examiner

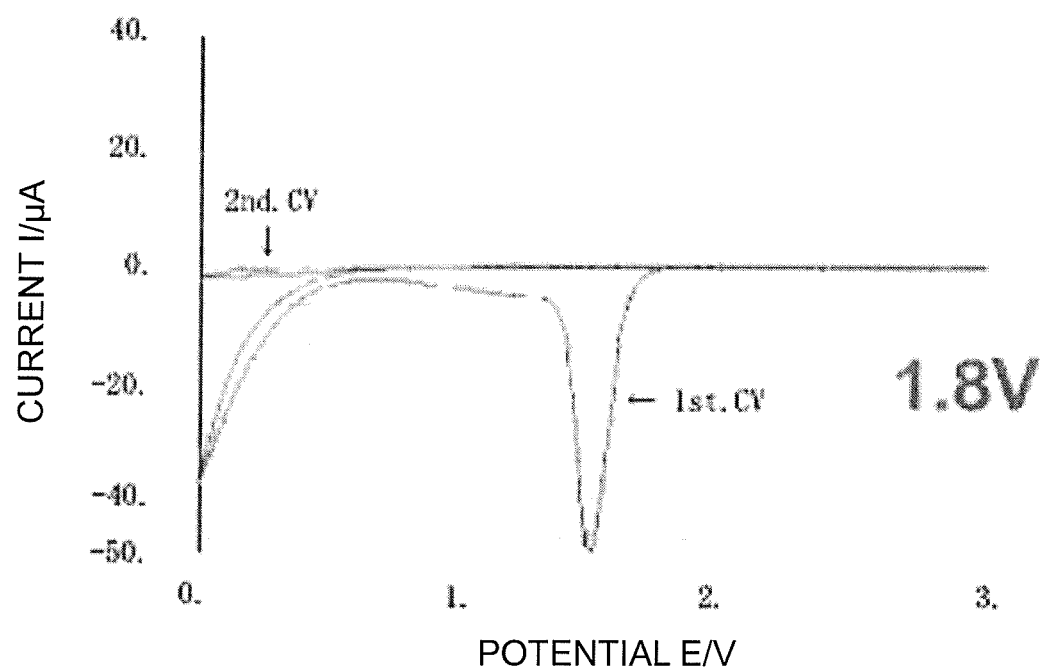

PROCESS FOR PRODUCTION OF BIS-QUATERNARY AMMONIUM SALT, AND NOVEL INTERMEDIATE

TECHNICAL FIELD

The present invention relates to a method for producing a bis-quaternary ammonium salt and a novel intermediate.

BACKGROUND ART

Bis-quaternary ammonium salts have been widely used as photosensitive silver halide photographic emulsions (Patent Literature 1, Patent Literature 2, and the like) and as antimicrobial agents and antimicrobial activity enhancing agents to exert antimicrobial activity against bacteria, eumycetes, and the like (Patent Literature 3, Patent Literature 4, and the like).

As for a method for producing a quaternary ammonium salt, for example, (1) a method in which a tertiary amine is reacted with an alkyl halide to generate a halogen salt of a quaternary ammonium and, thereafter, salt exchange with an organic acid salt is performed, so as to produce a desired quaternary ammonium salt (Patent Literature 5), (2) a method in which anion exchange is performed by using a halide salt of quaternary ammonium, phosphonium, imidazolium, or pyridinium and an acid or a salt thereof, so as to produce a desired ionic liquid (Patent Literature 6), and (3) a method in which a trialkyl amine is reacted with a carbonic acid diester to generate a quaternary ammonium alkali carbonate and, thereafter, a reaction with an organic carboxylic acid or phosphoric acid is effected, so as to produce a desired quaternary ammonium salt (Patent Literature 7 and Patent Literature 8) have been studied.

However, these methods have problems in that the number of steps are large and the operations are complicated because the halogen salt or the carbonate is generated as an intermediate and, thereafter, an anion exchange reaction to the desired anion is effected. Furthermore, the methods of the above-described items (1) and (2) have disadvantages that, for example, the halogen salt is formed as the intermediate, this exhibits skin irritation, so as to cause hand roughness of an operator and cause corrosion of instruments, containers, and the like, and has poor biodegradability.

Under such circumstances, a development of a method for efficiently producing a bis-quaternary ammonium salt exhibiting no skin irritation and a low level of metal corrosion behavior has been desired.

CITATION LIST

Patent Literatures

Patent Literature 1: Japanese Unexamined Patent Application Publication No. 6-242534
Patent Literature 2: Japanese Unexamined Patent Application Publication No. 2002-55407
Patent Literature 3: Japanese Unexamined Patent Application Publication No. 10-114604
Patent Literature 4: Japanese Unexamined Patent Application Publication No. 2004-217501
Patent Literature 5: Japanese Unexamined Patent Application Publication No. 2000-178104
Patent Literature 6: Japanese Unexamined Patent Application Publication (Translation of PCT Application) No. 2005-511666
Patent Literature 7: Japanese Unexamined Patent Application Publication No. 9-77610
Patent Literature 8: Japanese Unexamined Patent Application Publication No. 9-132504

DISCLOSURE OF THE INVENTION

Problems to be Solved by the Invention

The present invention has been made in consideration of the above-described circumstances, and it is an object to provide a method for producing a bis-quaternary ammonium salt efficiently.

Means for Solving the Problems

The present invention relates to a method for producing a bis-quaternary ammonium salt represented by a general formula [3] which comprises reacting a disulfonic acid ester represented by a general formula [1] with a tertiary amine represented by a general formula [2]:

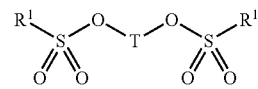

[1]

wherein, $R^1$ represents an alkyl group which may have a substituent, a haloalkyl group, a heteroatom-containing alkyl group which may have a substituent, an aryl group which may have a substituent, an aralkyl group which may have a substituent, a heterocyclic group which may have a substituent, or an unsaturated hydrocarbon group, and T represents an alkylene chain which may have a substituent or a heteroatom-containing alkylene chain;

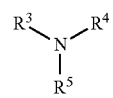

[2]

wherein, $R^3$ to $R^5$ represent independently an alkyl group or a heteroatom-containing alkyl group, $R^3$ and $R^4$ or $R^3$ to $R^5$ and a nitrogen atom bonding thereto may form a heterocycle;

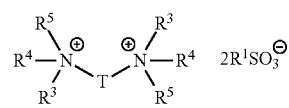

[3]

wherein, $R^1$, $R^3$ to $R^5$ and T are the same as the above, and relates to a disulfonic acid ester represented by a general formula [1']

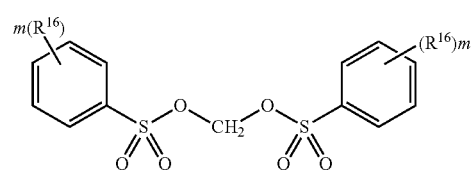

[1']

wherein, two $R^{16}$'s represent independently a halogen atom or a C1-C3 fluoroalkyl group, and two m's represent independently an integer of 1 to 5.

Effect of the Invention

According to the method for producing a bis-quaternary ammonium salt of the present invention, various types of bis-quaternary ammonium salts can be produced efficiently without having problems included in the conventional methods, for example, it is necessary to generate the halogen salt in advance before the anion exchange to the desired anion is effected and, thereby, the number of steps is large, the halogen salt exhibits skin irritation, and the halogen salt is not preferable because of corrosion of the equipment.

The bis-quaternary ammonium salt obtained by the method according to the present invention is suitable for photosensitive silver halide photographic emulsions, antimicrobial agents, and the like.

In the case where the novel disulfonic acid ester represented by the general formula [1'] according to the present invention is used as an additive to an electrolyte for a lithium ion secondary battery, an electrolyte capable of generating a stable passive film (SEI: solid electrolyte interface) with a small amount of charge consumption is produced, and by using this, a battery exhibiting excellent cycle characteristics and having a small irreversible capacity and a large charge and discharge capacity can be provided.

BRIEF DESCRIPTION OF THE DRAWINGS

FIG. 1 is a diagram showing a cyclic voltammogram with respect to a compound of Example 7.

BEST MODE FOR CARRYING OUT THE INVENTION

In the general formula [1], an alkyl group of the alkyl group which is represented by $R^1$ and which may have a substituent may be any one of straight-chain, branched, and cyclic alkyl groups. Most of all, a straight-chain group is preferable, and the alkyl group includes one having usually 1 to 20, preferably 1 to 12, and more preferably 1 to 10 carbon atoms. Concrete examples include a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a 1-methylpentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a n-undecyl group, an isoundecyl group, a sec-undecyl group, a tert-undecyl group, a neoundecyl group, a n-dodecyl group, an isododecyl group, a sec-dodecyl group, a tert-dodecyl group, a n-tridecyl group, an isotridecyl group, a sec-tridecyl group, a tert-tridecyl group, a neotridecyl group, a n-tetradecyl group, an isotetradecyl group, a sec-tetradecyl group, a tert-tetradecyl group, a neotetradecyl group, a n-pentadecyl group, an isopentadecyl group, a sec-pentadecyl group, a tert-pentadecyl group, a neopentadecyl group, a n-hexadecyl group, an isohexadecyl group, a sec-hexadecyl group, a tert-hexadecyl group, a neohexadecyl group, a n-heptadecyl group, an iso-heptadecyl group, a sec-heptadecyl group, a tert-heptadecyl group, a neoheptadecyl group, a n-octadecyl group, an isooctadecyl group, a sec-octadecyl group, a tert-octadecyl group, a neooctadecyl group, a n-nonadecyl group, an isononadecyl group, a sec-nonadecyl group, a tert-nonadecyl group, a neo-nonadecyl group, a n-icocyl group, an isoicocyl group, a sec-icocyl group, a tert-icocyl group, a neoicocyl group, a cyclopropyl group, a cyclobutyl group, a cyclopentyl group, a cyclohexyl group, a cycloheptyl group, a cyclooctyl group, a cyclononyl group, a cyclodecyl group, a cycloundecyl group, and a cyclododecyl group.

Examples of the substituent of the alkyl group, which is represented by $R^1$ and which may have a substituent, include an aryl group, an aralkyl group, an alkoxy group, an acyl group, an amino group which may have a substituent, a cyano group, a nitro group, a hydroxyl group, a carboxyl group, a formyl group, and a sulfo group.

Examples of the aryl group mentioned as the substituent include an aryl group having usually 6 to 14 carbon atoms. Concrete examples include a phenyl group, a naphthyl group, and an anthryl group.

Examples of the aralkyl group mentioned as the substituent include an aralkyl group having usually 7 to 12 carbon atoms. Concrete examples include a benzyl group, a phenethyl group, a phenylpropyl group, a phenylbutyl group, a phenylpentyl group, and a phenylhexyl group.

Examples of the alkoxy group mentioned as the substituent may be any one of straight-chain, branched, and cyclic alkoxy groups, and the alkoxy group includes one having usually 1 to 12, preferably 1 to 6, and more preferably 1 to 3 carbon atoms. Concrete examples include a methoxy group, an ethoxy group, a n-propoxy group, an isopropoxy group, a n-butoxy group, an isobutoxy group, a sec-butoxy group, a tert-butoxy group, a n-pentyloxy group, an isopentyloxy group, a sec-pentyloxy group, a tert-pentyloxy group, a neopentyloxy group, a n-hexyloxy group, an isohexyloxy group, a sec-hexyloxy group, a tert-hexyloxy group, a neohexyloxy group, a n-heptyloxy group, an isoheptyloxy group, a sec-heptyloxy group, a tert-heptyloxy group, a neoheptyloxy group, a n-octyloxy group, an isooctyloxy group, a sec-octyloxy group, a tert-octyloxy group, a neooctyloxy group, a n-nonyloxy group, an isononyloxy group, a sec-nonyloxy group, a tert-nonyloxy group, a neononyloxy group, a n-decyloxy group, an isodecyloxy group, a sec-decyloxy group, a tert-decyloxy group, a neodecyloxy group, a n-undecyloxy group, an isoundecyloxy group, a sec-undecyloxy group, a tert-undecyloxy group, a neoundecyloxy group, a n-dodecyloxy group, an isododecyloxy group, a sec-dodecyloxy group, a tert-dodecyloxy group, a neododecyloxy group, a cyclopropoxy group, a cyclobutoxy group, a cyclopentyloxy group, a cyclohexyloxy group, a cycloheptyloxy group, a cyclooctyloxy group, a cyclononyloxy group, a cyclodecyloxy group, a cycloundecyloxy group, and a cyclododecyloxy group.

Examples of the acyl group mentioned as the substituent include an acyl group derived from an aliphatic carboxylic acid and derived from an aromatic carboxylic acid.

Among the acyl groups mentioned as the substituent, the acyl group derived from the aliphatic carboxylic acid may be straight-chain, branched, or cyclic acyl groups, and furthermore, may have a double bond in the chain. The acyl group includes one having usually 1 to 20 and preferably 1 to 15 carbon atoms. Concrete examples include an acyl group derived from a saturated aliphatic carboxylic acid such as a formyl group, an acetyl group, a propionyl group, a butyryl group, an isobutyryl group, a valeryl group, an isovaleryl group, a pivaloyl group, a hexanoyl group, a heptanoyl group, an octanoyl group, a nonanoyl group, a decanoyl group, an undecanoyl group, a lauroyl group, a myristoyl group, a palmitoyl group, a stearoyl group, an icosanoyl group, and a cyclohexylcarbonyl group; and an acyl group derived from an unsaturated aliphatic carboxylic acid such as an acryloyl group, a methacryloyl group, a crotonoyl group, and an oleoyl group.

Among the acyl groups mentioned as the substituent, the acyl group derived from the aromatic carboxylic acid includes one having usually 7 to 15 and preferably 7 to 11 carbon atoms. Concrete examples include a benzoyl group, a naphthoyl group, a toluoyl group, and an anthroyl group.

Among the amino groups which are mentioned as the substituent and which may have a substituent, examples of the amino group having a substituent include an amino group in which one or two hydrogen atoms in the amino group are substituted with the substituent such as an alkyl group having 1 to 10 carbon atoms, an alkenyl group, an alkynyl group, an aryl group, an aralkyl group, an acyl group, an oxycarbonyl group, a sulfonyl group, and an alkylsilyl group.

The alkyl group, which has 1 to 10 carbon atoms and which is mentioned as the substituent of the amino group having a substituent, may be any one of straight-chain, branched, and cyclic alkyl groups. Concrete examples include a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a 1-methylpentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a cyclopropyl group, a cyclobutyl group, a cyclopentyl group, a cyclohexyl group, a cycloheptyl group, a cyclooctyl group, a cyclononyl group, a cyclodecyl group, and an adamantyl group.

The alkenyl group, which is mentioned as the substituent of the amino group having a substituent, may be any one of straight-chain, branched, and cyclic alkenyl groups, and the alkenyl group includes one having usually 2 to 12, and preferably 2 to 6 carbon atoms. Concrete examples include a vinyl group, an allyl group, a 1-propenyl group, an isopropenyl group, a 1-butenyl group, a 2-butenyl group, a 3-butenyl group, a 2-methylallyl group, a 1-pentenyl group, a 2-pentenyl group, a 3-pentenyl group, a 4-pentenyl group, a 2-methyl-2-butenyl group, a 1-hexenyl group, a 2-hexenyl group, a 3-hexenyl group, a 5-hexenyl group, a 2-methyl-2-pentenyl group, a 1-heptenyl group, a 2-heptenyl group, a 3-heptenyl group, a 4-heptenyl group, a 5-heptenyl group, a 6-heptenyl group, a 1-dodecenyl group, a 2-dodecenyl group, a 3-dodecenyl group, a 4-dodecenyl group, a 5-dodecenyl group, a 6-dodecenyl group, a 7-dodecenyl group, an 8-dodecenyl group, a 9-dodecenyl group, a 10-dodecenyl group, an 11-dodecenyl group, a 1-cyclobutenyl group, a 1-cyclopentenyl group, and a 1-cyclohexenyl group.

The alkynyl group, which is mentioned as the substituent of the amino group having a substituent, may be any one of straight-chain, branched, and cyclic alkynyl groups, and the alkynyl group includes one having usually 2 to 12, and preferably 2 to 6 carbon atoms. Concrete examples include an ethynyl group, a 1-propynyl group, a 2-propynyl group, a 1-butynyl group, a 2-butynyl group, a 3-butynyl group, a 1-methyl-2-propynyl group, a 1-pentynyl group, a 2-pentynyl group, a 3-pentynyl group, a 4-pentynyl group, a 1-methyl-3-butynyl group, a 1-hexynyl group, a 2-hexynyl group, a 3-hexynyl group, a 4-hexynyl group, a 5-hexynyl group, a 2-methyl-4-pentynyl group, a 1-heptynyl group, a 2-heptynyl group, a 3-heptynyl group, a 4-heptynyl group, a 5-heptynyl group, a 6-heptynyl group, a 1-octynyl group, a 2-octynyl group, a 3-octynyl group, a 4-octynyl group, a 5-octynyl group, a 6-octynyl group, a 7-octynyl group, a 1-nonynyl group, a 2-nonynyl group, a 3-nonynyl group, a 4-nonynyl group, a 5-nonynyl group, a 6-nonynyl group, a 7-nonynyl group, an 8-nonynyl group, a 1-decynyl group, a 3-decynyl group, a 5-decynyl group, a 7-decynyl group, a 9-decynyl group, a 1-undecynyl group, a 3-undecynyl group, a 5-undecynyl group, a 7-undecynyl group, a 9-undecynyl group, a 1-dodecynyl group, a 3-dodecynyl group, a 5-dodecynyl group, a 7-dodecynyl group, a 9-dodecynyl group, and an 11-dodecynyl group.

The aryl group mentioned as the substituent of the amino group having a substituent includes one having usually 6 to 14, and preferably 6 to 10 carbon atoms. Concrete examples include a phenyl group, a naphthyl group, a phenanthryl group, and an anthryl group.

The aralkyl group mentioned as the substituent of the amino group having a substituent includes one having usually 7 to 12 carbon atoms. Concrete examples include a benzyl group, a phenethyl group, a phenylpropyl group, a phenylbutyl group, a phenylpentyl group, and a phenylhexyl group.

Examples of the acyl group mentioned as the substituent of the amino group having a substituent include an acyl group derived from an aliphatic carboxylic acid, an aromatic carboxylic acid, an araliphatic carboxylic acid, and the like.

Among the acyl groups mentioned as the substituent of the amino group having the substituent, the acyl group derived from the aliphatic carboxylic acid may be straight-chain, branched, or cyclic acyl groups, and furthermore, may have a double bond in the chain. The acyl group includes one having usually 1 to 20, and preferably 1 to 15 carbon atoms. Concrete examples include an acyl group derived from a saturated aliphatic carboxylic acid such as a formyl group, an acetyl group, a propionyl group, a butyryl group, an isobutyryl group, a valeryl group, an isovaleryl group, a pivaloyl group, a hexanoyl group, a heptanoyl group, an octanoyl group, a nonanoyl group, a decanonyl group, an undecanoyl group, a lauroyl group, a tridecanoyl group, a myristoyl group, a pentadecanoyl group, a palmitoyl group, a heptadecanoyl group, a stearoyl group, a nonadecanoyl group, an icosanoyl group, and a cyclohexylcarbonyl group; a halogen-substituted acyl is group such as a chloroacetyl group, a trichloroacetyl group, a trifluoroacetyl group, and a chlorobutanoyl group; and an acyl group derived from an unsaturated carboxylic acid such as an acryloyl group, a methacryloyl group, a crotonoyl group, and an oleoyl group.

Among the acyl groups mentioned as the substituent of the amino group having the substituent, the acyl group derived from the aromatic carboxylic acid includes one having usually 7 to 16 and preferably 7 to 11 carbon atoms. Concrete examples include a benzoyl group, a nitrobenzoyl group, a p-phenylbenzoyl group, a naphthoyl group, a toluoyl group, and an anthroyl group.

Among the acyl groups mentioned as the substituent of the amino group having the substituent, the acyl group derived from the araliphatic carboxylic acid includes one having usually 8 to 16 carbon atoms. Concrete examples include a phenylacetyl group, a nitrophenylacetyl group, a phenylpropionyl group, and a nitrophenylpropionyl group.

Examples of the oxycarbonyl group mentioned as the substituent of the amino group having the substituent include an alkoxycarbonyl group having 1 to 4 carbon atoms such as a methoxycarbonyl group, an ethoxycarbonyl group, a tert-butoxycarbonyl group, and a 2,2,2-trichloroethoxycarbonyl group; an aralkyloxycarbonyl group such as a benzyloxycarbonyl group, and a 4-methoxybenzyloxycarbonyl group; a 9-fluorenylmethyloxycarbonyl group, and an allyloxycarbonyl group.

Examples of the sulfonyl group mentioned as the substituent of the amino group having the substituent include an alkylsulfonyl group having 1 to 4 carbon atoms such as a methanesulfonyl group, an ethanesulfonyl group, a propanesulfonyl group, a butanesulfonyl group, and a tert-butanesulfonyl group; and an arylsulfonyl group such as a p-toluenesulfonyl group and a benzenesulfonyl group.

The alkylsilyl group mentioned as the substituent of the amino group having a substituent includes an alkylsilyl group in which a part of or all hydrogen atoms of the silyl group are substituted with an alkyl group having 1 to 6, and preferably 1 to 4 carbon atoms. The alkyl group concerned may be any one of straight-chain, branched, and cyclic alkyl groups. Concrete examples include a methylsilyl group, an ethylsilyl group, a n-propylsilyl group, an isopropylsilyl group, a n-butylsilyl group, an isobutylsilyl group, a sec-butylsilyl group, a tert-butylsilyl group, a neobutylsilyl group, a n-pentylsilyl group, an isopentylsilyl group, a sec-pentylsilyl group, a tert-pentylsilyl group, a neopentylsilyl group, a n-hexylsilyl group, an isohexylsilyl group, a sec-hexylsilyl group, a tert-hexylsilyl group, a neohexylsilyl group, a cyclopropylsilyl group, a cyclobutylsilyl group, a cyclopentylsilyl group, a cyclohexylsilyl group, a dimethylsilyl group, a diethylsilyl group, a di-n-propylsilyl group, a diisopropylsilyl group, a di-n-butylsilyl group, a diisobutylsilyl group, a di-sec-butylsilyl group, a di-tert-butylsilyl group, a dineobutylsilyl group, a di-n-pentylsilyl group, a diisopentylsilyl group, a di-sec-pentylsilyl group, a di-tert-pentylsilyl group, a dineopentylsilyl group, a di-n-hexylsilyl group, a diisohexylsilyl group, a di-sec-hexylsilyl group, a di-tert-hexylsilyl group, a dineohexylsilyl group, a dicyclopropylsilyl group, a dicyclobutylsilyl group, a dicyclopentylsilyl group, a dicyclohexylsilyl group, a trimethylsilyl group, a triethylsilyl group, a tri-n-propylsilyl group, a triisopropylsilyl group, a tri-n-butylsilyl group, a triisobutylsilyl group, a tri-sec-butylsilyl group, a tri-tert-butylsilyl group, a trineobutylsilyl group, a tri-n-pentylsilyl group, a triisopentylsilyl group, a tri-sec-pentylsilyl group, a tri-tert-pentylsilyl group, a trineopentylsilyl group, a tri-n-hexylsilyl group, a triisohexylsilyl group, a tri-sec-hexylsilyl group, a tri-tert-hexylsilyl group, a trineohexylsilyl group, a tricyclopropylsilyl group, a tricyclobutylsilyl group, a tricyclopentylsilyl group, a tricyclohexylsilyl group, a dimethylethylsilyl group, a tert-butyldimethylsilyl group, a dimethylisopropylsilyl group, a diethylisopropylsilyl group, a pentyldimethylsilyl group, and a hexyldimethylsilyl group.

Typical concrete examples of the amino group having the substituent include an alkyl-substituted amino group such as a methylamino group, a dimethylamino group, an ethylamino group, a tert-butylamino group, and an adamantylamino group; an alkenyl-substituted amino group such as a vinylamino group and an allylamino group; an alkyl-substituted amide group such as a formamide group, an acetamide group, a chloroacetamide group, a trichloroacetamide group, a trifluoroacetamide group, a nitrophenylacetamide group, a nitrophenoxyacetamide group, a propanamide group, and a chlorobutanamide; an aryl-substituted amide group such as a benzamide group, a nitrobenzamide group, and a p-phenylbenzamide group; an aralkyl-substituted amide group such as a phenylacetamide group, a phenylpropanamide group, and a nitrophenylpropanamide group; an acyl-substituted amide group such as an acrylic amide group and a methacrylic amide group; an alkylsilyl-substituted amide group such as a trimethylsilylamide group, and a tert-butyldimethylsilylamide group; an oxycarbonyl-substituted amino group (carbamate group) such as a tert-butoxycarbonyl amino group, a benzyloxycarbonyl amino group, a 4-methoxybenzyloxycarbonyl amino group, and a 9-fluorenylmethyloxycarbonyl amino group; a sulfonyl-substituted amino group (sulfonamide group) such as a methane sulfonamide group, a trifluoromethane sulfonamide group, a benzene sulfonamide group, a naphthalene sulfonamide group, an anthracene sulfonamide group, a p-toluene sulfonamide group, and p-methoxyphenyl sulfonamide group; and an alkylsilyl-substituted amino group such as a trimethylsilylamino group, a triisopropylsilylamino group, and a tert-butyldimethylsilyl amino group.

In the general formula [1], the haloalkyl group represented by $R^1$ may be any one of straight-chain, branched, and cyclic haloalkyl groups, and includes a haloalkyl group in which a part of or all hydrogen atoms of the alkyl group having usually 1 to 12, preferably 1 to 6, and more preferably 1 to 3 carbon atoms are substituted with a halogen atom (for example, a fluorine atom, a chlorine atom, a bromine atom, or an iodine atom is mentioned). Concrete examples include a fluoromethyl group, a chloromethyl group, a bromomethyl group, an iodomethyl group, a trifluoromethyl group, a trichloromethyl group, a tribromomethyl group, a 2-fluoroethyl group, a 2-chloroethyl group, a 2-bromoethyl group, a pentafluoroethyl group, a pentachloroethyl group, a pentabromoethyl group, a pentaiodoethyl group, a 3-fluoropropyl group, a 3-chloropropyl group, a 3-bromopropyl group, a trifluoropropyl group, a trichloropropyl group, a tribromopropyl group, a di(trifluoromethyl)methyl group, a di(trichloromethyl)methyl group, a di(tribromomethyl)methyl group, a heptafluoropropyl group, a heptachloropropyl group, a 4-fluorobutyl group, a 4-chlorobutyl group, a 4-bromobutyl group, a nonafluorobutyl group, a nonachlorobutyl group, a nonabromobutyl group, a 5-fluoropentyl group, a 5-chloropentyl group, a 5-bromopentyl group, a 2,2,3,3,4,4,5,5-octafluoropentyl group ($-CH_2(CF_2)_4H$), a 2,2,3,3,4,4,5,5-octachloropentyl group ($-CH_2(CCl_2)_4H$), a 2,2,3,3,4,4,5,5-octabromopentyl group ($-CH_2(CBr_2)_4H$), a perfluoropentyl group, a perchloropentyl group, a perbromopentyl group, a 6-fluorohexyl group, a 6-chlorohexyl group, a 6-bromohexyl group, a perfluorohexyl group, a perchlorohexyl group, a perbromohexyl group, a perfluoroheptyl group, a perchloroheptyl group, a perbromoheptyl group, a perfluorooctxyl group, a perchlorooctyl group, a perbromooctyl group, a perfluorononyl group, a perchlorononyl group, a perbromononyl group, a 3,3,4,4,5,5,6,6,7,7,8,8,9,9,10,10,10-heptadecafluorodecyl group ($-(CH_2)_2(CF_2)_7CF_3$), a 3,3,4,4,5,5,6,6,7,7,8,8,9,9,10,10,10-heptadecachlorodecyl group ($-(CH_2)_2(CCl_2)_7CCl_3$), a 3,3,4,4,5,5,6,6,7,7,8,8,9,9,10,10,10-heptadecabromodecyl group ($-(CH_2)_2(CBr_2)_7CBr_3$), a perfluorodecyl group, a perchlorodecyl group, a perbromodecyl group, a perfluoroundecyl group, a perchloroundecyl group, a perbromoundecyl group, a perfluorododecyl group, a perchlorododecyl group, and a perbromododecyl group.

The heteroatom-containing alkyl group of the heteroatom-containing alkyl group which is represented by $R^1$ and which may have a substituent includes one having usually 1 to 6, and preferably 1 to 4 heteroatoms in the chain of the alkyl group which may have a substituent. Concrete examples include a group represented by a general formula [4]

[4]

{in the formula, $R^6$ represents an alkyl group which may have a substituent, $T_1$'s, where the number thereof is m, represent independently an alkylene chain which has 1 to 8 carbon atoms and which may have a substituent, $X_1$'s, where the number thereof is m, represent independently an oxygen atom, a sulfur atom, or a general formula [5]

[5]

(in the formula, $R^7$ represents an alkyl group, a haloalkyl group, an aryl group, or an aralkyl group), and m represents an integer of 1 to 6}.

In the general formula [4], the alkyl group of the alkyl group which is represented by $R^6$ and which may have a substituent may be any one of straight-chain, branched, and cyclic alkyl groups, and the alkyl group includes one having usually 1 to 20, preferably 1 to 6, and more preferably 1 to 3 carbon atoms. Concrete examples include a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a 1-methylpentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a n-undecyl group, an isoundecyl group, a sec-undecyl group, a tert-undecyl group, a neoundecyl group, a n-dodecyl group, an isododecyl group, a sec-dodecyl group, a tert-dodecyl group, a neododecyl group, a cyclopropyl group, a cyclobutyl group, a cyclopentyl group, a cyclohexyl group, a cycloheptyl group, a cyclooctyl group, a cyclononyl group, a cyclodecyl group, a cycloundecyl group, and a cyclododecyl group.

The alkylene chain of the alkylene chain represented by $T_1$ which have 1 to 8 carbon atoms and which may have the substituent includes a straight-chain alkylene group having usually 1 to 8, and preferably 1 to 3 carbon atoms. Concrete examples include a methylene group, an ethylene group, a trimethylene group, a tetramethylene group, a pentamethylene group, a hexamethylene group, a heptamethylene group, and an octamethylene group.

Examples of the substituent of the alkyl group represented by $R^6$ which may have the substituent and the substituent of the alkylene chain represented by $T_1$ which have 1 to 8 carbon atoms and which may have the substituent include a halogen atom, a haloalkyl group, an alkyl group, an aryl group, an alkoxy group, an acyl group, a nitro group, a hydroxyl group, a carboxyl group, a cyano group, a formyl group, and a sulfo group.

Examples of the halogen atom mentioned as the substituent include a fluorine atom, a chlorine atom, a bromine atom, and an iodine atom.

The haloalkyl group mentioned as the substituent may be any one of straight-chain, branched, and cyclic haloalkyl groups, and includes a haloalkyl group in which a part of or all hydrogen atoms of the alkyl group having 1 to 12, preferably 1 to 6, and more preferably 1 to 3 carbon atoms are substituted with a halogen atom (for example, a fluorine atom, a chlorine atom, a bromine atom, or an iodine atom is mentioned). Concrete examples include the same haloalkyl group as the exemplifications of the haloalkyl group which is represented by $R^1$ in the general formula [1] and which has 1 to 12 carbon atoms.

The alkyl group mentioned as the substituent may be any one of straight-chain, branched, and cyclic alkyl groups, and includes one having usually 1 to 12, preferably 1 to 6, and more preferably 1 to 3 carbon atoms. Concrete examples include the same alkyl group as the exemplifications of the alkyl group having 1 to 12 carbon atoms of the alkyl group which is represented by $R^1$ in the general formula [1] and which may have the substituent.

Examples of the aryl group, the alkoxy group, and the acyl group include the same aryl group, alkoxy group, and acyl group as the exemplifications mentioned as the substituent of the alkyl group which is represented by $R^1$ in the general formula [1] and which may have the substituent.

In the general formula [5], the alkyl group represented by $R^7$ may be any one of straight-chain, branched, and cyclic alkyl groups, and includes one having usually 1 to 12, preferably 1 to 6, and more preferably 1 to 3 carbon atoms. Concrete examples include the same alkyl group as the exemplifications of the alkyl group having 1 to 12 carbon atoms of the alkyl group which is represented by $R^1$ in the general formula [1] and which may have substituent.

The haloalkyl group represented by $R^7$ may be any one of straight-chain, branched, and cyclic haloalkyl groups, and includes a haloalkyl group in which a part of or all hydrogen atoms of the alkyl group having usually 1 to 12, preferably 1 to 6, and more preferably 1 to 3 carbon atoms are substituted with a halogen atom (for example, a fluorine atom, a chlorine atom, a bromine atom, or an iodine atom is mentioned). Concrete examples include the same haloalkyl group as the exemplifications of the haloalkyl group which is represented by $R^1$ in the general formula [1] and which has 1 to 12 carbon atoms.

The aryl group represented by $R^7$ includes one having usually 6 to 14 carbon atoms. Concrete examples include a phenyl group, a naphthyl group, and an anthryl group.

The aralkyl group represented by $R^7$ includes one having usually 7 to 15 carbon atoms. Concrete examples include a benzyl group, a phenethyl group, a phenylpropyl group, a phenylbutyl group, a phenylpentyl group, a phenylhexyl group, a phenylheptyl group, a phenyloctyl group, a phenylnonyl group, and a naphthylmethyl group.

In the general formula [4], m represents an integer of usually 1 to 6, and preferably 1 to 3. Furthermore, $X_1$'s and $T_1$'s, where the numbers thereof are m, may be the same or be different.

In the general formula [1], the aryl group of the aryl group which is represented by $R^1$ and which may have a substituent includes one having usually 6 to 14, and preferably 6 to 10 carbon atoms. Concrete examples include a phenyl group, a naphthyl group, a phenanthryl group, and an anthryl group.

The aralkyl group of the aralkyl group which is represented by $R^1$ and which may have a substituent includes one having usually 7 to 15 carbon atoms. Concrete examples include a benzyl group, a phenethyl group, a phenylpropyl group, a phenylbutyl group, a phenylpentyl group, a phenylhexyl group, a phenylheptyl group, a phenyloctyl group, a phenylnonyl group, and a naphthylmethyl group.

The heterocyclic group of the heterocyclic group which is represented by $R^1$ and which may have a substituent includes one having a heterocyclic ring including at least one heteroatom, and preferably 1 to 3 heteroatoms, wherein at least one hydrogen atom is present on the heterocyclic ring.

The heteroatom included in the heterocyclic ring includes usually a nitrogen atom, an oxygen atom, a sulfur atom, and the like. Most of all, the nitrogen atom is preferable.

The heterocyclic ring described above includes a monocyclic heterocyclic ring or a polycyclic heterocyclic ring, which may have aromaticity and which is composed of usually 3 to 20 members, preferably 3 to 14 members, and more preferably 5 to 10 members. Furthermore, as for the monocyclic heterocyclic ring, 5 or 6-membered ring is preferable. Meanwhile, as for the polycyclic heterocyclic ring, 9 or 10-membered ring and, in particular, 9-membered ring is preferable. They may have a two-dimensional structure or a three-dimensional structure, in which rings are condensed into a chain shape, a branched shape, or an annular shape.

Moreover, the heterocyclic ring may have the substituent, the number of which is usually 1 to 5, preferably 1 or 2, and more preferably 1.

Examples of the monocyclic heterocyclic ring include a 3-membered heterocyclic ring having one heteroatom such as an oxirane ring and an aziridine ring; a 5-membered heterocyclic ring having one heteroatom such as a furan ring, a thiophene ring, a pyrrole ring, a 2H-pyrrole ring, a pyrroline ring, a 2-pyrroline ring, and a pyrrolidine ring; a 5-membered heterocyclic ring having two heteroatoms such as a 1,3-dioxolane ring, an oxazole ring, an isoxazole ring, a 1,3-oxazole ring, a thiazole ring, an isothiazole ring, a 1,3-thiazole ring, an imidazole ring, an imidazoline ring, a 2-imidazoline ring, an imidazolidine ring, a pyrazole ring, a pyrazoline ring, a 3-pyrazoline ring, and a pyrazolidine ring; a 5-membered heterocyclic ring having three heteroatoms such as a furazan ring, a triazole ring, a thiadiazole ring, and an oxadiazole ring; a 6-membered heterocyclic ring having one heteroatom such as a pyran ring, a 2H-pyran ring, a thiopyran ring, a pyridine ring, and a piperidine ring; a 6-membered heterocyclic ring having two heteroatoms such as a pyridazine ring, a pyrimidine ring, a pyrazine ring, a piperazine ring, and a morpholine ring; and a 6-membered heterocyclic ring having three heteroatoms such as a 1,2,4-triazine ring.

Examples of the polycyclic heterocyclic ring include a ring in which 2 or 3 monocyclic heterocyclic rings are condensed with each other, and a bicyclic heterocyclic ring and a tricyclic heterocyclic ring, which are produced by condensation of a monocyclic heterocyclic ring with one or two aromatic rings such as a benzene ring and a naphthalene ring.

Examples of the bicyclic heterocyclic ring include a heterocyclic ring having one heteroatom such as a benzofuran ring, an isobenzofuran ring, a 1-benzothiophene ring, a 2-benzothiophene ring, an indole ring, a 3-indole ring, an isoindole ring, an indolizine ring, an indoline ring, an isoindolinone ring, a 2H-chromene ring, a chroman ring, an isochroman ring, a 1H-2-benzopyran ring, a quinoline ring, an isoquinoline ring, and a 4H-quinolizine ring; a heterocyclic ring having two heteroatoms such as a benzimidazole ring, a benzothiazole ring, a 1H-indazole ring, a 1,8-naphthylidine ring, a quinoxaline ring, a quinazoline ring, a quinazolidine ring, a cinnoline ring, and a phthalazine ring; and a heterocyclic ring having four heteroatoms such as a purine ring and a pteridine ring.

Examples of the tricyclic heterocyclic ring include a heterocyclic ring having one heteroatom such as a carbazole ring, a 4aH-carbazole ring, a xanthene ring, a phenanthridine ring, and an acridine ring; and a heterocyclic ring having two heteroatoms such as a β-carboline ring, a perimidine ring, a 1,7-phenanthroline ring, a 1,10-phenanthroline ring, a thianthrene ring, a phenoxathiin ring, a phenoxazine ring, a phenothiazine ring, and a phenazine ring.

Examples of the substituent of the heteroatom-containing alkyl group or the heterocyclic group, which is represented by $R^1$ and which may have the substituent, include a halogen atom, an aryl group, an aralkyl group, an alkoxy group, an acyl group, an amino group which may have a substituent, a cyano group, a nitro group, a hydroxyl group, a carboxyl group, a formyl group, and a sulfo group.

Examples of the substituent of the aryl group or the aralkyl group, which is represented by $R^1$ and which may have the substituent, include a halogen atom, an alkyl group, a haloalkyl group, an aryl group, an aralkyl group, an alkoxy group, an aryloxy group, a trialkylsilyloxy group, an acyl group, an acyloxy group, an alkoxycarbonyl group, an amino group which may have a substituent, a vinyl group, a cyano group, a nitro group, a hydroxyl group, a carboxyl group, a formyl group, and a sulfo group.

Examples of the aryl group, the aralkyl group, the alkoxy group, the acyl group, and the amino group which may have the substituent, these group being mentioned as the substituent, include the same aryl group, aralkyl group, alkoxy group, acyl group, and amino group which may have the substituent as the exemplifications mentioned as the substituent of the alkyl group which is represented by $R^1$ in the general formula [1] and which may have the substituent.

Examples of the halogen atom mentioned as the substituent include a fluorine atom, a chlorine atom, a bromine atom, and an iodine atom.

The alkyl group mentioned as the substituent may be any one of straight-chain, branched, and cyclic alkyl groups, and includes one having usually 1 to 12, and preferably 1 to 8 carbon atoms. Concrete examples include the same alkyl group as the exemplifications of the alkyl group having 1 to 12 carbon atoms of the alkyl group which is represented by $R^1$ in the general formula [1] and which may have the substituent.

The haloalkyl group mentioned as the substituent may be any one of straight-chain, branched, and cyclic haloalkyl groups, and includes a haloalkyl group in which a part of or all hydrogen atoms of the alkyl group having 1 to 12, preferably 1 to 6, and more preferably 1 to 3 carbon atoms are substituted with a halogen atom (for example, a fluorine atom, a chlorine atom, a bromine atom, or an iodine atom is mentioned). Concrete examples include the same haloalkyl group as the exemplifications of the haloalkyl group having 1 to 12 carbon atoms of the haloalkyl group which is represented by $R^1$ in the general formula [1] and which may have the substituent.

The aryloxy group mentioned as the substituent includes one having usually 6 to 14 carbon atoms. Concrete examples include a phenyloxy group, a naphthyloxy group, and an anthryloxy group.

Examples of the trialkylsilyloxy group mentioned as the substituent include a group in which three hydrogen atoms of a silyloxy group are substituted with an alkyl group having 1 to 21 carbon atoms, an aryl group, or an aralkyl group.

The alkyl group in the case where a hydrogen atom of the silyloxy group is substituted with the alkyl group may be any one of straight-chain, branched, and cyclic alkyl groups, and includes one having usually 1 to 21, and preferably 1 to 15 carbon atoms. Concrete examples include a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a 1-methylpentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, a is neooctyl group, a n-nonyl group, an isononyl group, a sec-nonyl group, a Cert-nonyl group, a neononyl group, a n-decyl group, an isodecyl group, a sec-decyl group, a tert-decyl group, a neodecyl group, a n-undecyl group, an isoundecyl group, a sec-undecyl group, a tert-undecyl group, a neoundecyl group, a n-dodecyl group, an isododecyl group, a sec-dodecyl group, a tert-dodecyl group, a n-tridecyl group, an isotridecyl group, a sec-tridecyl group, a tert-tridecyl group, a neotridecyl group, a n-tetradecyl group, an isotetradecyl group, a sec-tetradecyl group, a tert-tetradecyl group, a neotetradecyl group, a n-pentadecyl group, an isopentadecyl group, a sec-pentadecyl group, a tert-pentadecyl group, a neopentadecyl group, a n-hexadecyl group, an isohexadecyl group, a sec-hexadecyl group, a tert-hexadecyl group, a neohexadecyl group, a n-heptadecyl group, an isoheptadecyl group, a sec-heptadecyl group, a tert-heptadecyl group, a neoheptadecyl group, a n-octadecyl group, an isooctadecyl group, a sec-octadecyl group, a tert-octadecyl group, a neooctadecyl group, a n-nonadecyl group, an isononadecyl group, a sec-nonadecyl group, a tert-nonadecyl group, a neononadecyl group, a n-icocyl group, an isoicocyl group, a sec-icocyl group, a tert-icocyl group, a neoicocyl group, a n-henicocyl group, an isohenicocyl group, a sec-henicocyl group, a tert-henicocyl group, a neohenicocyl group, a cyclopropyl group, a cyclobutyl group, a cyclopentyl group, a cyclohexyl group, a cycloheptyl group, a cyclooctyl group, a cyclononyl group, a cyclodecyl group, a cycloundecyl group, and a cyclododecyl group.

The aryl group in the case where a hydrogen atom of the silyloxy group is substituted with the aryl group includes one having usually 6 to 10 carbonatoms. Concrete examples include a phenyl group and a naphthyl group.

The aralkyl group in the case where a hydrogen atom of the silyloxy group is substituted with the aralkyl group includes one having usually 7 to 10 carbon atoms. Concrete examples include a benzyl group, a phenethyl group, a phenylpropyl group, and a phenylbutyl group.

Preferable concrete examples of the trialkylsilyloxy group include a trialkylsilyloxy group such as a trimethylsilyloxy group, a triethylsilyloxy group, a tri-n-propylsilyloxy group, a triisopropylsilyloxy group, a tri-n-butylsilyloxy group, a triisobutylsilyloxy group, a tri-sec-butylsilyloxy group, a tri-tert-butylsilyloxy group, a tri-n-pentylsilyloxy group, a triisopentylsilyloxy group, a tri-sec-pentylsilyloxy group, a tri-tert-pentylsilyloxy group, a trineopentylsilyloxy group, a tri-n-hexylsilyloxy group, a triisohexylsilyloxy group, a tri-sec-hexylsilyloxy group, a tri-tert-hexylsilyloxy group, a trineohexylsilyloxy group, a tri-n-heptylsilyloxy group, a tri-isoheptylsilyloxy group, a tri-sec-heptylsilyloxy group, a tri-tert-heptylsilyloxy group, a trineoheptylsilyloxy group, a tri-n-octylsilyloxy group, a triisooctylsilyloxy group, a tri-sec-octylsilyloxy group, a tri-tert-octylsilyloxy group, a trineooctylsilyloxy group, a tri-n-nonylsilyloxy group, a tri-isononylsilyloxy group, a tri-sec-nonylsilyloxy group, a tri-tert-nonylsilyloxy group, a trineononylsilyloxy group, a tri-n-decylsilyloxy group, a triisodecylsilyloxy group, a tri-sec-decylsilyloxy group, a tri-tert-decylsilyloxy group, a trineodecylsilyloxy group, a tri-n-undecylsilyloxy group, a triisoundecylsilyloxy group, a tri-sec-undecylsilyloxy group, a tri-tert undecylsilyloxy group, a trineoundecylsilyloxy group, a tri-n-dodecylsilyloxy group, a triisododecylsilyloxy group, a tri-sec-dodecylsilyloxy group, a tri-tert-dodecylsilyloxy group, a trineododecylsilyloxy group, a tri-n-tridecylsilyloxy group, a triisotridecylsilyloxy group, a tri-sec-tridecylsilyloxy group, a tri-tert-tridecylsilyloxy group, a trineotridecylsilyloxy group, a tri-n-tetradecylsilyloxy group, a triisotetradecylsilyloxy group, a tri-sec-tetradecylsilyloxy group, a tri-tert-tetradecylsilyloxy group, a trineotetradecylsilyloxy group, a tri-n-pentadecylsilyloxy group, a triisopentadecylsilyloxy group, a tri-sec-pentadecylsilyloxy group, a tri-tert-pentadecylsilyloxy group, a trineopentadecylsilyloxy group, a tri-n-hexadecylsilyloxy group, a triisohexadecylsilyloxy group, a tri-sec-hexadecylsilyloxy group, a tri-tert-hexadecylsilyloxy group, a trineohexadecylsilyloxy group, a tri-n-heptadecylsilyloxy group, a triisoheptadecylsilyloxy group, a tri-sec-heptadecylsilyloxy group, a tri-tert-heptadecylsilyloxy group, a trineoheptadecylsilyloxy group, a tri-n-octadecylsilyloxy group, a triisooctadecylsilyloxy group, a tri-sec-octadecylsilyloxy group, a tri-tert-octadecylsilyloxy group, a trineooctadecylsilyloxy group, a tri-n-nonadecylsilyloxy group, a triisononadecylsilyloxy group, a tri-sec-nonadecylsilyloxy group, a tri-tert-nonadecylsilyloxy group, a trineononadecylsilyloxy group, a tri-n-icocylsilyloxy group, a triisoicocylsilyloxy group, a tri-sec-icocylsilyloxy group, a tri-tert-cocylsilyloxy group, a trineoicocylsilyloxy group, a tri-n-henicocylsilyloxy group, a triisohenicocylsilyloxy group, a tri-sec-henicocylsilyloxy group, a tri-tert-henicocylsilyloxy group, a trineohenicocylsilyloxy group, a tricyclopropylsilyloxy group, a tricyclobutylsilyloxy group, a tricyclopentylsilyloxy group, a tricyclohexylsilyloxy group, a tricycloheptylsilyloxy group, and a tricyclooctylsilyloxy group; a triarylsilyloxy group such as a triphenyloxy group; a triaralkylsilyloxy group such as a tribenzylsilyloxy group; and an alkyldiarylsilyloxy group such as a tert-butyldiphenylsilyloxy group.

Examples of the acyloxy group mentioned as the substituent include an acyloxy group in which a hydrogen atom of a hydroxyl group has been substituted with an acyl group. Examples include an acyloxy group derived from an aliphatic carboxylic acid and an aromatic carboxylic acid.

Among the acyloxy groups mentioned as the substituent, the acyloxy group derived from the aliphatic carboxylic acid may be any one of straight-chain, branched, and cyclic acyloxy groups, and furthermore, may have a double bond in the chain. The acyloxy group includes one having usually 1 to 20 and preferably 1 to 15 carbon atoms. Concrete examples include an acyloxy group derived from a saturated aliphatic carboxylic acid such as a formyloxy group, an acetyloxy group, a propionyloxy group, a butyryloxy group, an isobutyryloxy group, a valeryloxy group, an isovaleryloxy group, a pivaloyloxy group, a hexanoyloxy group, a heptanoyloxy group, an octanoyloxy group, a nonanoyloxy group, a decanoyloxy group, an undecanoyloxy group, a lauroyloxy group, a myristoyloxy is group, a palmitoyloxy group, a stearoyloxy group, an icosanoyloxy group, and a cyclohexyl carbonyloxy group; and an acyloxy group derived from an unsaturated aliphatic carboxylic acid such as an acryloyloxy group, a methacryloyloxy group, a crotonoyloxy group, and an oleoyloxy group.

Among the acyloxy groups mentioned as the substituent, the acyloxy group derived from the aromatic carboxylic acid includes one having usually 7 to 15, and preferably 7 to 11 carbon atoms. Concrete examples include a benzoyloxy group, a naphthoyloxy group, a toluoyloxy group, and an anthroyloxy group.

Examples of the alkoxycarbonyl group mentioned as the substituent include an alkoxycarbonyl group in which a hydroxyl group in a carboxyl group has been substituted with an alkoxy group. The alkoxycarbonyl group may be any one of straight-chain, branched, and cyclic alkoxycarbonyl groups, and the alkoxycarbonyl group includes one having usually 1 to 12, and preferably 1 to 6 carbon atoms. Concrete examples include a methoxycarbonyl group, an ethoxycarbonyl group, a n-propoxycarbonyl group, an isopropoxycarbonyl group, a n-butoxycarbonyl group, an isobutoxycarbonyl group, a sec-butoxycarbonyl group, a tert-butoxycarbonyl group, a n-pentyloxycarbonyl group, an isopentyloxycarbonyl group, a sec-pentyloxycarbonyl group, a tert-pentyloxycarbonyl group, a neopentyloxycarbonyl group, a n-hexyloxycarbonyl group, an isohexyloxycarbonyl group, a sec-hexyloxycarbonyl group, a tert-hexyloxycarbonyl group, a neohexyloxycarbonyl group, a n-heptyloxycarbonyl group, an isoheptyloxycarbonyl group, a sec-heptyloxycarbonyl group, a tert-heptyloxycarbonyl group, a neoheptyloxycarbonyl group, a n-octyloxycarbonyl group, an isooctyloxycarbonyl group, a sec-octyloxycarbonyl group, a tert-octyloxycarbonyl group, a neooctyloxycarbonyl group, a n-nonyloxycarbonyl group, an isononyloxycarbonyl group, a sec-nonyloxycarbonyl group, a tert-nonyloxycarbonyl group, a neononyloxycarbonyl group, a n-decyloxycarbonyl group, an isodecyloxycarbonyl group, a sec-decyloxycarbonyl group, a tert-decyloxycarbonyl group, a neodecyloxycarbonyl group, a n-undecyloxycarbonyl group, an isoundecyloxycarbonyl group, a sec-undecyloxycarbonyl group, a tert-undecyloxycarbonyl group, a neoundecyloxycarbonyl group, a n-dodecyloxycarbonyl group, an isododecyloxycarbonyl group, a sec-dodecyloxycarbonyl group, a tert-dodecyloxycarbonyl group, a neododecyloxycarbonyl group, a cyclopropoxycarbonyl group, a cyclobutoxycarbonyl group, a cyclopentyloxycarbonyl group, and a cyclohexyloxycarbonyl group.

In the general formula [1], typical concrete examples of the aryl group, which is represented by $R^1$ and which has a substituent, include an alkyl-substituted aryl group such as a tolyl group and a xylyl group; an amino-substituted aryl group such as an aminophenyl group and an aminonaphthyl group; and an acylamino-substituted aryl group such as a benzylaminophenyl group, a phenoxycarbonylaminophenyl group, a benzamide phenyl group, an acrylaminophenyl group, and a methacrylaminophenyl group.

In the general formula [1], examples of the unsaturated hydrocarbon group represented by $R^1$ include a group represented by a general formula [6]

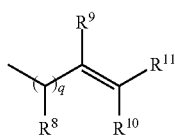

[6]

(in the formula, $R^8$ to $R^{11}$ represent independently a hydrogen atom, an alkyl group, or an aryl group, and q represents an integer of 0 to 2).

In the general formula [6], the alkyl group represented by $R^8$ to $R^{11}$ may be any one of straight-chain, branched, and cyclic alkyl groups. Most of all, the straight-chain group is preferable, and the alkyl group includes one having usually 1 to 6 carbon atoms. Concrete examples include a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a 1-methylpentyl group, a n-hexyl group, an isohexyl group, a sec-hexyl group, a tert-hexyl group, a neohexyl group, a cyclopropyl group, a cyclobutyl group, a cyclopentyl group, and a cyclohexyl group.

The aryl group represented by $R^8$ to $R^{11}$ includes one having usually 6 to 14, and preferably 6 to 10 carbon atoms. Concrete examples include a phenyl group, a naphthyl group, a phenanthryl group, and an anthryl group.

A letter q represents an integer of usually 0 to 2, and preferably 0 or 1.

Preferable concrete examples of the group represented by the general formula [6] include an allyl group, a 2-methylallyl group, and a cinnamyl group.

In the general formula [1], the alkylene chain of the alkylene chain which is represented by T and which may have a substituent may be straight-chain type or branched type, and the alkylene chain includes an alkylene group having usually 1 to 20, preferably 1 to 18, and more preferably 6 to 18 carbon atoms. Concrete examples include a methylene group, an ethylene group, a trimethylene group, a tetramethylene group, a pentamethylene group, a hexamethylene group, a heptamethylene group, an octamethylene group, a nonamethylene group, a decamethylene group, an undecamethylene group, a dodecamethylene group, a tridecamethylene group, a tetradecamethylene group, a pentadecamethylene group, a hexadecamethylene group, a heptadecamethylene group, an octadecamethylene group, a nonadecamethylene group, and an icosamethylene group.

Examples of the substituent of the alkylene chain which may have the substituent include a halogen atom, an alkyl group, a haloalkyl group, an aryl group, a cyano group, a nitro group, a hydroxyl group, a carboxyl group, a formyl group, and a sulfo group. Concrete examples thereof include the same halogen atom, alkyl group, haloalkyl group, and aryl group as the exemplifications mentioned as the substituent of the aryl group or the aralkyl group which is represented by $R^1$ in the general formula [1] and which may have the substituent.

The heteroatom-containing alkylene chain represented by T includes a chain having usually 1 to 6, and preferably 1 to 4 heteroatoms in the alkylene chain. Concrete examples include a group represented by a general formula [19]

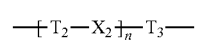

[19]

(in the formula, $T_2$ and $T_3$ represent independently an alkylene chain having 1 to 8 carbon atoms, $X_2$ represents an oxygen atom or a sulfur atom, and n represents an integer of 1 to 5).

In the general formula [19], the alkylene chain which is represented by $T_2$ and $T_3$ and which has 1 to 8 carbon atoms includes a straight-chain alkylene chain having usually 1 to 8, and preferably 2 to 4 carbon atoms. Concrete examples include a methylene group, an ethylene group, a trimethylene group, a tetramethylene group, a pentamethylene group, a hexamethylene group, a heptamethylene group, and an octamethylene group.

A letter n represents an integer of usually 1 to 5, and preferably 1 to 3.

In the general formula [2], the alkyl group represented by $R^3$ or $R^4$ may be any one of straight-chain, branched, and cyclic alkyl groups, and includes one having usually 1 to 20, and preferably 1 to 12 carbon atoms. Concrete examples include a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a 1-methylpentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a n-undecyl group, an isoundecyl group, a sec-undecyl group, a tert-undecyl group, a neoundecyl group, a n-dodecyl group, an isododecyl group, a sec-dodecyl group, a tert-dodecyl group, a neododecyl group, a n-tridecyl group, an isotridecyl group, a sec-tridecyl group, a tert-tridecyl group, a neotridecyl group, a n-tetradecyl group, an isotetradecyl group, a sec-tetradecyl group, a tert-tetradecyl group, a neotetradecyl group, a n-pentadecyl group, an isopentadecyl group, a sec-pentadecyl group, a tert-pentadecyl group, a neopentadecyl group, a n-hexadecyl group, an isohexadecyl group, a sec-hexadecyl group, a tert-hexadecyl group, a neohexadecyl group, a n-heptadecyl group, an isoheptadecyl group, a sec-heptadecyl group, a tert-heptadecyl group, a neoheptadecyl group, a n-octadecyl group, an isooctadecyl group, a sec-octadecyl group, a tert-octadecyl group, a neooctadecyl group, a n-nonadecyl group, an isononadecyl group, a sec-nonadecyl group, a tert-nonadecyl group, a neononadecyl group, a n-icocyl group, an isoicocyl group, a sec-icocyl group, a tert-icocyl group, a neoicocyl group, a cyclopropyl group, a cyclobutyl group, a cyclopentyl group, a cyclohexyl group, a cycloheptyl group, a cyclooctyl group, a cyclononyl group, a cyclodecyl group, a cycloundecyl group, a cyclododecyl group, a cyclotridecyl group, a cyclopentadecyl group, a cyclohexadecyl group, a cycloheptadecyl group, and a cyclooctadecyl group.

The alkyl group represented by $R^5$ may be any one of straight-chain, branched, and cyclic alkyl groups, and the alkyl group includes one having usually 1 to 20, preferably 1 to 18, and more preferably 6 to 18 carbon atoms. Concrete examples include the same alkyl group as the exemplifications of the above-described alkyl group represented by $R^3$ and $R^4$.

The heteroatom-containing alkyl group represented by $R^3$ to $R^5$ includes the same heteroatom-containing alkyl group as the exemplifications of the heteroatom-containing alkyl group which is represented by $R^1$ and $R^2$ in the general formula [1] and which may have the substituent.

The heterocycle formed from $R^3$ and $R^4$ or $R^3$ to $R^5$ and a nitrogen atom bonding thereto is, for example, a 5-membered ring or a 6-membered ring and may contain one or two heteroatoms (for example, a nitrogen atom, an oxygen atom, and a sulfur atom) besides one nitrogen atom. Concrete examples include a pyrrole ring, an imidazoline ring, a pyrazoline ring, a pyrroline ring, a piperidine ring, a piperazine ring, a morpholine ring, a thiazoline ring, a pyridine ring, a pyrazine ring, a pyrimidine ring, a pyridazine ring, an imidazole ring, a pyrazole ring, an oxazole ring, a thiazole ring, a furan ring, a pyran ring, a pyrrolidine ring, a quinoline ring, an isoquinoline ring, a quinoxaline ring, an indole ring, an isoindolinone ring, and a carbazole ring.

The heterocycle may further have an alkyl group, a haloalkyl group, an aryl group, an aralkyl group, or an unsaturated hydrocarbon group represented by the general formula [6] as a substituent. Preferable concrete examples of the heterocyclic compound having such substituent include a heterocyclic compound represented by general formulae [7] to [14]

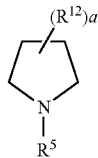

[7]

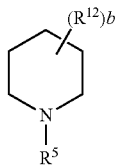

[8]

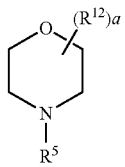

[9]

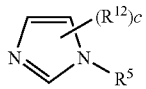

[10]

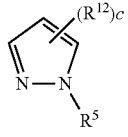

[11]

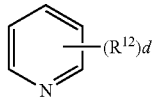

[12]

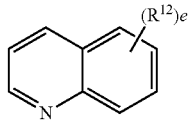

[13]

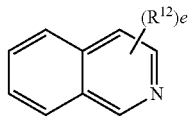

[14]

(in the formulae, $R^{12}$ represents an alkyl group, a haloalkyl group, an aryl group, an aralkyl group, or an unsaturated hydrocarbon group represented by the general formula [6], a represents an integer of 1 to 8, b represents an integer of 1 to 10, c represents an integer of 1 to 3, d represents an integer of 1 to 5, e represents an integer of 1 to 7, and $R^5$ is the same as that described above).

In the general formulae [7] to [14], the alkyl group represented by $R^{12}$ may be any one of straight-chain, branched, and cyclic alkyl groups, and includes one having usually 1 to 20, preferably 1 to 18, and more preferably 6 to 18 carbon atoms. Concrete examples include the same alkyl group as the exemplifications of the alkyl group represented by $R^5$ in the general formula [2].

The haloalkyl group represented by $R^{12}$ may be any one of straight-chain, branched, and cyclic haloalkyl groups, and includes a haloalkyl group in which a part of or all hydrogen atoms of the alkyl group having usually 1 to 20, preferably 1 to 18, and more preferably 6 to 18 carbon atoms are substituted with a halogen atom (for example, a fluorine atom, a chlorine atom, a bromine atom, or an iodine atom is mentioned). Concrete examples include the same haloalkyl group as the exemplifications of the haloalkyl group which is represented by $R^5$ in the general formula [2].

The aryl group represented by $R^{12}$ includes one having usually 6 to 14 carbon atoms. Concrete examples include a phenyl group, a naphthyl group, and an anthryl group.

The aralkyl group represented by $R^{12}$ includes one having usually 7 to 15 carbon atoms. Concrete examples include a benzyl group, a phenethyl group, a phenylpropyl group, and a naphthylmethyl group.

In the general formulae [7] and [9], a represents an integer of usually 1 to 8, preferably 1 to 4, and more preferably 1 or 2.

In the general formula [8], b represents an integer of usually 1 to 10, preferably 1 to 4, and more preferably 1 or 2.

In the general formulae [10] and [11], c represents an integer of usually 1 to 3, and preferably 1 or 2.

In the general formula [12], d represents an integer of usually 1 to 5, preferably 1 to 3, and more preferably 1 or 2.

In the general formulae [13] and [14], e represents an integer of usually 1 to 7, preferably 1 to 3, and more preferably 1 or 2.

Concrete examples of the compound represented by the general formula [7] include 1-methylpyrrolidine, 1-ethylpyrrolidine, 1-propylpyrrolidine, 1-butylpyrrolidine, 1-pentylpyrrolidine, 1-hexylpyrrolidine, 1-heptylpyrrolidine, 1-octylpyrrolidine, 1-nonylpyrrolidine, 1-decylpyrrolidine, 1-undecylpyrrolidine, and 1-dodecylpyrrolidine.

Concrete examples of the compound represented by the general formula [8] include 1-methylpiperidine, 1-ethylpiperidine, 1-propylpiperidine, 1-butylpiperidine, 1-pentylpiperidine, 1-hexylpiperidine, 1-heptylpiperidine, 1-octylpiperidine, 1-nonylpiperidine, 1-decylpiperidine, 1-undecylpiperidine, and 1-dodecylpiperidine.

Concrete examples of the compound represented by the general formula [9] include 4-methylmorpholine, 4-ethylmorpholine, 4-propylmorpholine, 4-butylmorpholine, 4-pentylmorpholine, 4-hexylmorpholine, 4-heptylmorpholine, 4-octylmorpholine, 4-nonylmorpholine, 4-decylmorpholine, 4-undecylmorpholine, and 4-dodecylmorpholine.

Concrete examples of the compound represented by the general formula [10] include 1-methylimidazole, 1-ethylimidazole, 1-propylimidazole, 1-butylimidazole, 1-pentylimidazole, 1-hexylimidazole, 1-heptylimidazole, 1-octylimidazole, 1-nonylimidazole, 1-decylimidazole, 1-undecylimidazole, and 1-dodecylimidazole.

Concrete examples of the compound represented by the general formula [11] include 1-methylpyrazole, 1-ethyl pyrazole, 1-propylpyrazole, 1-butylpyrazole, 1-pentylpyrazole, 1-hexylpyrazole, 1-heptylpyrazole, 1-octylpyrazole, 1-nonylpyrazole, 1-decylpyrazole, 1-undecylpyrazole, 1-dodecylpyrazole, 1-methyl-3,5-dimethylpyrazole, 1-ethyl-3,5-dimethylpyrazole, 1-propyl-3,5-dimethylpyrazole, 1-butyl-3,5-dimethylpyrazole, 1-pentyl-3,5-dimethylpyrazole, 1-hexyl-3,5-dimethylpyrazole, 1-heptyl-3,5-dimethylpyrazole, 1-octyl-3,5-dimethylpyrazole, 1-nonyl-3,5-dimethylpyrazole, 1-decyl-3,5-dimethylpyrazole, 1-undecyl-3,5-dimethylpyrazole, and 1-dodecyl-3,5-dimethylpyrazole.

Concrete examples of the compound represented by the general formula [12] include 2-methylpyridine, 3-methylpyridine, 4-methylpyridine, 5-methylpyridine, 6-methylpyridine, 2-ethylpyridine, 3-ethylpyridine, 4-ethylpyridine, 5-ethylpyridine, 6-ethylpyridine, 2-propylpyridine, 3-propylpyridine, 4-propylpyridine, 5-propylpyridine, 6-propylpyridine, 2-butylpyridine, 3-butylpyridine, 4-butylpyridine, 5-butylpyridine, 6-butylpyridine, 2-pentylpyridine, 3-pentylpyridine, 4-pentylpyridine, 5-pentylpyridine, 6-pentylpyridine, 2-hexylpyridine, 3-hexylpyridine, 4-hexylpyridine, 5-hexylpyridine, 6-hexylpyridine, 2-heptylpyridine, 3-heptylpyridine, 4-heptylpyridine, 5-heptylpyridine, 6-heptylpyridine, 2-octylpyridine, 3-octylpyridine, 4-octylpyridine, 5-octylpyridine, 6-octylpyridine, 2-nonylpyridine, 3-nonylpyridine, 4-nonylpyridine, 5-nonylpyridine, 6-nonylpyridine, 2-decylpyridine, 3-decylpyridine, 4-decylpyridine, 5-decylpyridine, 6-decylpyridine, 2-undecyl pyridine, 3-undecylpyridine, 4-undecylpyridine, 5-undecylpyridine, 6-undecylpyridine, 2-dodecylpyridine, 3-dodecylpyridine, 4-dodecylpyridine, 5-dodecylpyridine, 6-dodecylpyridine, 2,3-lutidine, 2,4-lutidine, 2,5-lutidine, 2,6-lutidine, 3,4-lutidine, 3,5-lutidine, 2,4,6-collidine, α-collidine (4-ethyl-2-methylpyridine), β-collidine (3-ethyl-2-methylpyridine), and γ-collidine (2,4,6-collidine).

Concrete examples of the compound represented by the general formula [13] include 2-methylquinoline, 3-methylquinoline, 4-methylquinoline, 5-methylquinoline, 6-methylquinoline, 7-methylquinoline, 8-methylquinoline, 2-ethylquinoline, 3-ethylquinoline, 4-ethylquinoline, 5-ethylquinoline, 6-ethylquinoline, 7-ethylquinoline, 8-ethylquinoline, 2-propylquinoline, 3-propylquinoline, 4-propylquinoline, 5-propylquinoline, 6-propylquinoline, 7-propylquinoline, 8-propylquinoline, 2-butylquinoline, 3-butylquinoline, 4-butylquinoline, 5-butylquinoline, 6-butylquinoline, 7-butylquinoline, 8-butylquinoline, 2-pentylquinoline, 3-pentylquinoline, 4-pentylquinoline, 5-pentylquinoline, 6-pentylquinoline, 7-pentylquinoline, 8-pentylquinoline, 2-hexylquinoline, 3-hexylquinoline, 4-hexylquinoline, 5-hexylquinoline, 6-hexylquinoline, 7-hexylquinoline, 8-hexylquinoline, 2-heptylquinoline, 3-heptylquinoline, 4-heptylquinoline, 5-heptylquinoline, 6-heptylquinoline, 7-heptylquinoline, 8-heptylquinoline, 2-octylquinoline, 3-octylquinoline, 4-octylquinoline, 5-octylquinoline, 6-octylquinoline, 7-octylquinoline, 8-octylquinoline, 2-nonylquinoline, 3-nonylquinoline, 4-nonylquinoline, 5-nonylquinoline, 6-nonylquinoline, 7-nonylquinoline, 8-nonylquinoline, 2-decylquinoline, 3-decylquinoline, 4-decylquinoline, 5-decylquinoline, 6-decylquinoline, 7-decylquinoline, 8-decylquinoline, 2-undecylquinoline, 3-undecylquinoline, 4-undecylquinoline, 5-undecylquinoline, 6-undecylquinoline, 7-undecylquinoline, 8-undecylquinoline, and 2-dodecylquinoline, 3-dodecylquinoline, 4-dodecylquinoline, 5-dodecylquinoline, 6-dodecylquinoline, 7-dodecylquinoline, 8-dodecylquinoline.

Concrete examples of the compound represented by the general formula [14] include 1-methylisoquinoline, 3-methylisoquinoline, 4-methylisoquinoline, 5-methylisoquinoline, 6-methylisoquinoline, 7-methylisoquinoline, 8-methylisoquinoline, 1-ethylisoquinoline, 3-ethylisoquinoline, 4-ethylisoquinoline, 5-ethylisoquinoline, 6-ethylisoquinoline, 7-ethylisoquinoline, 8-ethylisoquinoline, 1-propylisoquinoline, 3-propylisoquinoline, 4-propylisoquinoline, 5-propylisoquinoline, 6-propylisoquinoline, 7-propylisoquinoline, 8-propylisoquinoline, 1-butylisoquinoline, 3-butylisoquinoline, 4-butylisoquinoline, 5-butylisoquinoline, 6-butylisoquinoline, 7-butylisoquinoline, 8-butylisoquinoline, 1-pentylisoquinoline, 3-pentylisoquinoline, 4-pentylisoquinoline, 5-pentylisoquinoline, 6-pentylisoquinoline, 7-pentylisoquinoline, 8-pentylisoquinoline, 1-hexylisoquinoline, 3-hexylisoquinoline, 4-hexylisoquinoline, 5-hexylisoquinoline, 6-hexylisoquinoline, 7-hexylisoquinoline, 8-hexylisoquinoline, 1-heptylisoquinoline, 3-heptylisoquinoline, 4-heptylisoquinoline, 5-heptylisoquinoline, 6-heptylisoquinoline, 7-heptylisoquinoline, 8-heptylisoquinoline, 1-octylisoquinoline, 3-octylisoquinoline, 4-octylisoquinoline, 5-octylisoquinoline, 6-octylisoquinoline, 7-octylisoquinoline, 8-octylisoquinoline, 1-nonylisoquinoline, 3-nonylisoquinoline, 4-nonylisoquinoline, 5-nonylisoquinoline, 6-nonylisoquinoline, 7-nonylisoquinoline, 8-nonylisoquinoline, 1-decylisoquinoline, 3-decylisoquinoline, 4-decylisoquinoline, 5-decylisoquinoline, 6-decylisoquinoline, 7-decylisoquinoline, 8-decylisoquinoline, 1-undecylisoquinoline, 3-undecylisoquinoline, 4-undecylisoquinoline, 5-undecylisoquinoline, 6-undecylisoquinoline, 7-undecylisoquinoline, 8-undecylisoquinoline, and 1-dodecylisoquinoline, 3-dodecylisoquinoline, 4-dodecylisoquinoline, 5-dodecylisoquinoline, 6-dodecylisoquinoline, 7-dodecylisoquinoline, and 8-dodecylisoquinoline.

Typical concrete examples of the tertiary amine represented by the general formula [2] include tertiary alkylamines such as trimethylamine, triethylamine, tri-n-propylamine, tri-isopropylamine, tri-n-butylamine, triisobutylamine, tri-sec-butylamine, tri-tert-butylamine, tri-n-pentylamine, triisopentylamine, tri-sec-pentylamine, tri-tert-pentylamine, trineopentylamine, tri-hexylamine, triisohexylamine, tri-sec-hexylamine, tri-tert-hexylamine, trineohexylamine, tricyclopropylamine, tricyclobutylamine, tricyclopentylamine, tricyclohexylamine, dimethylethylamine, and diisopropylethylamine; tertiary aryl amines such as a triphenylamine and trinaphthylamine; tertiary aralkylamines such as tribenzylamine; and the above-described concrete examples of the compounds represented by the general formulae [7] to [14].

Typical concrete example of the disulfonic acid ester represented by the general formula [1] include methylene bis(methanesulfonate), methylene bis(trifluoromethanesulfonate), methylene bis(ethanesulfonate), methylene bis(n-butanesulfonate), methylene bis(octanesulfonate), methylene bis(3-methoxypropanesulfonate ), methylene bis(benzylsulfonate), methylene bis(2-benzoyloxyethanesulfonate ), methylene bis(vinylsulfonate), methylene bis(allylsulfonate), methylene bis(2-methylallylsulfonate), methylene bis(styrylsulfonate), methylene bis(cinnamylsulfonate), methylene bis(benzenesulfonate) methylene bis(4-methylbenzenesulfonate), methylene bis(2,4,6-trimethylbenzenesulfonate), methylene bis(4-methoxybenzenesulfonate), methylene bis(4-phenylbenzenesulfonate), methylene bis(4-phenoxybenzenesulfonate), methylene bis(4-vinylbenzenesulfonate), methylene bis(4-trimethylsilyloxybenzenesulfonate), methylene bis(3-methoxycarbonylbenzenesulfonate), methylene bis(4-acetoxybenzenesulfonate), methylene bis(3-nitrobenzenesulfonate), methylene bis(4-fluorobenzenesulfonate), methylene bis(4-chlorobenzenesulfonate), methylene bis(4-bromobenzenesulfonate), methylene bis(4-iodobenzenesulfonate), methylene bis(2,4-difluorobenzenesulfonate), methylene bis(2,6-difluorobenzenesulfonate), methylene bis(3,4-difluorobenzenesulfonate), methylene bis(2,5-dichlorobenzenesulfonate), methylene bis(3,5-dichlorobenzenesulfonate), methylene bis (2,3-dichlorobenzenesulfonate), methylene bis(2,4-dibromobenzenesulfonate), methylene bis(3-chloro-4-fluorobenzenesulfonate), methylene bis(4-bromo-2-chlorobenzenesulfonate), methylene bis(3,4,5-trifluorobenzenesulfonate), methylene bis(2,4,5-trifluorobenzenesulfonate), methylene bis(2,3,4-trifluorobenzenesulfonate), methylene bis(2,4,5-trichlorobenzenesulfonate), methylene bis(2,4,6-trichlorobenzenesulfonate), methylene bis(3,4,5-trichlorobenzenesulfonate), methylene bis(2-chloro-4,5-difluorobenzenesulfonate), methylene bis(4-bromo-2,5-difluorobenzenesulfonate), methylene bis(4-bromo-2,6-dichlorobenzenesulfonate), methylene bis (pentafluorobenzenesulfonate), methylene bis(3-trifluoromethylbenzenesulfonate), methylene bis(2-trifluoromethylbenzenesulfonate), methylene bis(4-trifluormethylbenzenesulfonate), methylene bis(2-chloro-4-trifluoromethylbenzenesulfonate), methylene bis(2-chloro-5-trifluoromethylbenzenesulfonate), methylene bis(4-chloro-2-trifluoromethylbenzenesulfonate), methylene bis (4-bromo-2-trifluoromethylbenzenesulfonate), methylene bis(2-brmo-5-trifluoromethylbenzenesulfonate), methylene bis(2,6-dichloro-4-trifluoromethylbenzenesulfonate), methylene bis(2,5-di-trifluoromethylbenzenesulfonate), methylene bis(2,4-di-trifluoromethylbenzenesulfonate), methylene bis(2-naphthalenesulfonate), methylene bis(1-naphthalenesulfonate), methylene bis(2-(6-methoxy)naphthalenesulfonate), methylene bis(2-(4-methoxy)naphthalenesulfonate), methylene bis(2-thienylsulfonate), 1,2-bis (methanesulfonyloxy)ethane, and 1,4-bis (methanesulfonyloxy)butane.

Concrete examples of typical cation section of the quaternary ammonium salt represented by the general formula [3] include a methylene bis(trimethylammonium) cation, a methylene bis(tri-n-butylammonium) cation, a methylene bis(1-methylpiperidinium) cation, a methylene bispyridinium cation, a methylene bis(3,5-dimethylpyridinium) cation, a methylene bis(3-methylpyridinium) cation, a methylene bisquinolium cation, a methylene bis(1,2-dimethylimidazolium) cation, a methylene bis(1-butylimidazolium) cation, a methylene bis(1-methylimidazolium) cation, an ethylene bispyridinium cation, an ethylene bis(3-methylpyridinium) cation, an ethylene bis(1-butylimidazolium) cation, an ethylene bis(1-methylimidazolium) cation, a trimethylene bispyridinium cation, a trimethylene bis(3,5-dimethylpyridinium) cation, a trimethylene bis(3-pyridinium) cation, a trimethylene bis(1-butylimidazolium) cation, a trimethylene bis(1-methylimidazolium) cation, a 3-oxapentyl bis(3-decylpyridinium) cation, a 4-oxahexyl bis(3-decylpyridinium) cation, a 5-oxanonyl bis(3-decylpyridinium) cation, a 3,6,9-trioxaundecyl bis(3-decylpyridinium) cation, a 3,6,9,12-tetraoxatetradecyl bis(3-decylpyridinium) cation, a 3-oxapentyl bis (1-decylimidazolium) cation, a 4-oxahexyl bis(1-decylimidazolium) cation, a 5-oxanonyl bis(1-decylimidazolium) cation, a 3,6,9-trioxaundecyl bis(1-decylimidazolium) cation, a 3,6,9,12-tetraoxatetradecyl bis (1-decylimidazoliurn) cation, a 3-thiapentyl bis(3-decylpyridinium) cation, a 4-thiahexyl bis(3-decylpyridinium) cation, a 5-thianonyl bis(3-decylpyridinium) cation, a 3,6,9-trithiaundecyl bis(3-decylpyridinium) cation, a 3,6,9,12-tetrathiatetradecyl bis(3-decylpyridinium) cation, a 3-thiapentyl bis(1-decylimidazolium) cation, a 4-thiahexyl bis(1- decylimidazolium) cation, a 5-thianonyl bis(1-decylimidazolium) cation, a 3,6,9-trithiaundecyl bis(1-decylimidazolium) cation, and a 3,6,9,12-tetrathiatetradecyl bis(1-decylimidazolium) cation.

Among the disulfonic acid esters represented by the general formula [1], a compound represented by the following general formula [1']

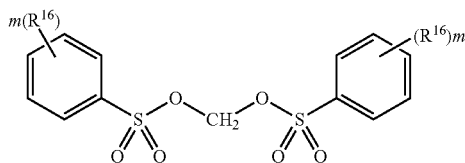

[1']

(in the formula, two $R^{16}$'s represent independently a halogen atom or a fluoroalkyl group having 1 to 3 carbon atoms and two m's represent independently an integer of 1 to 5) is novel compound.

In the general formula [1'], examples of halogen atom represented by $R^{16}$ include a fluorine atom, a chlorine atom, a bromine atom, and an iodine atom. Most of all, the fluorine atom, the chlorine atom, the bromine atom, and the like are preferable and, in particular, the fluorine atom is more preferable.

The fluoroalkyl group which is represented by $R^{16}$ and which has 1 to 3 carbon atoms may be any one of straight-chain, branched, and cyclic fluoloalkyl groups. Most of all, the straight-chain fluoloalkyl group is preferable. The fluorolkyl group includes a fluoroalkyl group in which a part of or all hydrogen atoms of the alkyl group having usually 1 to 3, preferably 1 or 2, and more preferably 1 carbon atoms are substituted with a fluorine atom. Most of all, a perfluoroalkyl group is preferable. Concrete examples of the fluoroalkyl group include a fluoromethyl group, a difluoromethyl group, a trifluoromethyl group, a fluoroethyl group, a difluoroethyl group, a trifluoroethyl group, a pentafluoroethyl group, a fluoropropyl group, a difluoropropyl group, a trifluoropropyl group, a pentafluoropropyl group, and a heptafluoropropyl group. Most of all, the trifluoromethyl group, the pentafluoroethyl group, the heptafluoropropyl group, and the like are preferable. In particular, the trifluoromethyl group is more preferable.

A letter m represents an integer of usually 1 to 5, preferably 1 to 3, and more preferably 1 or 2.

Preferable typical examples of the compound represented by the general formula [1] include methylene bis(4-fluorobenzenesulfonate), methylene bis(4-chlorobenzenesulfonate), methylene bis(4-bromobenzenesulfonate), methylene bis(4-iodobenzenesulfonate), methylene bis(2,4-difluorobenzenesulfonate), methylene bis(2,6-difluorobenzenesulfonate), methylene bis(3,4-difluorobenzenesulfonate), methylene bis(2,5-dichlorobenzenesulfonate), methylene bis(3,5-dichlorobenzenesulfonate), methylene bis(2,3-dichlorobenzenesulfonate), methylene bis(2,4-di bromobenzenesulfonate), methylene bis(3-chloro-4-fluorobenzenesulfonate), methylene bis(4-bromo-2-chlorobenzenesulfonate), methylene bis(3,4,5-trifluorobenzenesulfonate), methylene bis(2,4,5-trifluorobenzenesulfonate), methylene bis(2,3,4-trifluorobenzenesulfonate), methylene bis(2,4,5-trichlorobenzenesulfonate), methylene bis(2,4,6-trichlorobenzenesulfonate), methylene bis(3,4,5-trichlorobenzenesulfonate), methylene bis(2-chloro-4,5-difluorobenzenesulfonate), methylene bis(4-bromo-2,5-difluorobenzenesulfonate), methylene bis(4-bromo-2,6-dichlorobenzenesulfonate), methylene bis (pentafluorobenzenesulfonate), methylene bis(3-trifluoromethylbenzenesulfonate), methylene bis(2-trifluoromethylbenzenesulfonate), methylene bis(4-trifluoromethylbenzenesulfonate), methylene bis(2-chloro-4-trifluoromethylbenzenesulfonate), methylene bis(2-chloro-5-trifluoromethylbenzenesulfonate), methylene bis (4-chloro-2-trifluoromethylbenzenesulfonate), methylene bis(4-bromo-2-trifluoromethylbenzenesulfonate), methylene bis(2-bromo-5-trifluoromethylbenzenesulfonate), methylene bis(2,6-dichloro-4-trifluoromethylbenzenesulfonate), methylene bis(2,5-di-trifluoromethylbenzenesulfonate), and methylene bis(2,4-di-trifluoromethylbenzenesulfonate). Most of all, methylene bis(4-chlorobenzenesulfonate), methylene bis(2,5-dichlorobenzenesulfonate), methylene bis(3,5-dichlorobenzenesulfonate), methylene bis(4-fluorobenzenesulfonate), methylene bis(2,4-difluorobenzenesulfonate), methylene bis(pentafluorobenzenesulfonate), methylene bis (3-chloro-4-fluorobenzenesulfonate), methylene bis(4-trifluoromethylbenzenesulfonate), methylene bis(3-trifluoromethylbenzenesulfonate), methylene bis(2-trifluoromethylbenzenesulfonate).

In the case where the novel disulfonic acid ester represented by the general formula [1'] according to the present invention is used as, for example, an additive to an electrolyte for a lithium ion secondary battery, a stable passive film (SEI: solid electrolyte interface) is formed on a negative electrode of the battery and, thereby, reductive decomposition of a solvent on the negative electrode surface is prevented during charging. Consequently, an effect of preventing hindrance of occlusion and release of lithium in the electrolyte is exerted.

Meanwhile, consumption of charge is usually required to form a passive film (SEI: solid electrolyte interface). If the amount of this charge consumption is large, the irreversible capacity of the battery increases, so as to degrade the performance of the battery. Therefore, it is desired that an electrolyte which can form a stable passive film (SEI: solid electrolyte interface) with a minimum amount of charge consumption is provided. In the case where the novel disulfonic acid ester concerned is added to an electrolyte, reductive decomposition is effected with an amount of charge consumption smaller than that of the conventional additive, so as to form a passive film (SEI: solid electrolyte interface). That is, regarding a lithium ion secondary battery by using an electrolyte containing the disulfonic acid ester concerned, an irreversible capacity is reduced and, as a result, an effect of increasing a charge and discharge capacity is exerted.

The bis-quaternary ammonium salt represented by the general formula [3] according to the present invention is produced as described below, for example.

That is, the desired bis-quaternary ammonium salt represented by the general formula [3] is produced by mixing the disulfonic acid ester represented by the general formula [1] and the tertiary amine represented by the general formula [2] in an amount 2 to 5 times the amount of the disulfonic acid ester concerned on a mol basis and effecting a reaction under agitation in no solvent or an appropriate solvent at 0° C. to 200° C. for 0.5 to 24 hours.

As for the reaction solvent used, a nonaqueous solvent is preferable. Concrete examples include aliphatic hydrocarbons such as hexane, heptane, octane, isooctane, nonane, decane, undecane, dodecane, tridecane, tetradecane, pentadecane, hexadecane, heptadecane, octadecane, cyclohexane, methylcyclohexane, and ethylcyclohexane, or mixtures thereof (for example, paraffin, mineral spirit, and the like);

halogenated hydrocarbons such as methylene chloride, methylene bromide, 1,2-dichloroethane, and chloroform; aromatic hydrocarbons such as benzene, toluene, and xylene; carbonates such as dimethyl carbonate, diethyl carbonate, ethylene carbonate, and propylene carbonate; esters such as methyl acetate, ethyl acetate, and butyl acetate; ketones such as acetone and methyl ethyl ketone; ethers such as diethyl ether, isopropyl ether, cyclopentyl methyl ether, tetrahydrofuran, and dioxane; acetonitrile, dimethylformamide, dimethylacetamide, and dimethyl sulfoxide. They may be used alone or at least two types may be used in combination appropriately.

The reaction temperature is usually 0° C. to 200° C., and preferably 20° C. to 120° C.

The reaction time is usually 0.5 to 24 hours, and preferably 0.5 to 12 hours.

An aftertreatment after the reaction may be performed on the basis of the aftertreatment method usually employed in this field.

The compound represented by the general formula [1] may be synthesized appropriately on the basis of the usual method (for example, International Publication No. WO2008/032463). Concretely, the production can be performed as described below.

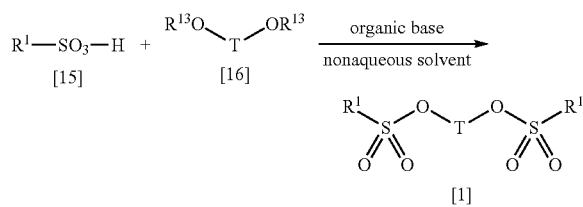

{in the formula, two $R^{13}$'s represent independently a sulfonyl group represented by a general formula [17]

(in the formula, $R^{14}$ represents a halogen atom, a haloalkyl group, an alkoxy group, or an alkyl group or an aryl group, which may have a substituent) or an acyl group represented by a general formula [18]

(in the formula, $R^{15}$ represents an alkyl group or an aryl group, which may have a substituent) and $R^1$ and T are the same as those described above}.

In the general formula [17], examples of a halogen atom represented by $R^{14}$ include a fluorine atom, a chlorine atom, a bromine atom, and an iodine atom.

The haloalkyl group represented by $R^{14}$ may be any one of straight-chain, branched, and cyclic haloalkyl groups, and includes a haloalkyl group in which a part of or all hydrogen atoms of the alkyl group having usually 1 to 12, preferably 1 to 6, and more preferably 1 to 3 carbon atoms are substituted with a halogen atom (for example, a fluorine atom, a chlorine atom, a bromine atom, or an iodine atom is mentioned). Concrete examples include the same haloalkyl group as the exemplifications of the haloalkyl group which is represented by $R^1$ in the general formula [1] and which has 1 to 12 carbon atoms.

The alkoxy group represented by $R^{14}$ may be any one of straight-chain, branched, and cyclic alkoxy groups, and includes one having usually 1 to 12, preferably 1 to 6, and more preferably 1 to 3 carbon atoms. Concrete examples include the same alkoxy group as the exemplifications of the alkoxy group having 1 to 12 carbon atoms of the alkoxy group which is represented by $R^1$ in the general formula [1] and which may have the substituent.

The alkyl group of the alkyl group which is represented by $R^{14}$ and $R^{15}$ and which may have the substituent may be any one of straight-chain, branched, and cyclic alkyl groups, and the alkyl group includes one having usually 1 to 12, preferably 1 to 6, and more preferably 1 to 3 carbon atoms. Concrete examples include the same alkyl group as the exemplifications of the alkyl group having 1 to 12 carbon atoms of the alkyl group which is represented by $R^1$ in the general formula [1] and which may have the substituent.

The aryl group of the aryl group which is represented by $R^{14}$ and $R^{15}$ and which may have the substituent includes one having usually 6 to 14, and preferably 6 to 10 carbon atoms. Concrete examples include a phenyl group, a naphthyl group, a phenanthryl group, and an anthryl group.

Examples of the substituent of the alkyl group which is represented by $R^{14}$ and which may have the substituent include an alkoxy group having 1 to 12 carbon atoms, an acyl group, a nitro group, a hydroxyl group, a carboxyl group, a cyano group, and a formyl group.

Examples of the substituent of the alkyl group which is represented by $R^{15}$ and which may have the substituent include a halogen atom, an alkoxy group having 1 to 12 carbon atoms, an acyl group, a nitro group, a hydroxyl group, a carboxyl group, a cyano group, and a formyl group.

Examples of the substituent of the aryl group which is represented by $R^{14}$ and $R^{15}$ and which may have the substituent include a halogen atom, an alkyl group having 1 to 12 carbon atoms, an alkoxy group having 1 to 12 carbon atoms, an acyl group, a nitro group, a hydroxyl group, a carboxyl group, a cyano group, and a formyl group.

Examples of a halogen atom mentioned as the substituent include a fluorine atom, a chlorine atom, a bromine atom, and an iodine atom.

The alkoxy group which is mentioned as the substituent and which has 1 to 12 carbon atoms may be any one of straight-chain, branched, and cyclic alkoxy groups, and the alkoxy group includes one having usually 1 to 12, preferably 1 to 6, and more preferably 1 to 3 carbon atoms. Concrete examples include the same alkoxy group as the exemplifications of the alkoxy group having 1 to 12 carbon atoms and being mentioned as the substituent of the alkoxy group which is represented by $R^1$ in the general formula [1] and which may have the substituent.

The acyl group mentioned as the substituent includes an acyl group which has usually 2 to 20 carbon atoms and which is derived from the carboxylic acid. Concrete examples include the same acyl group as the exemplifications of the acyl group mentioned as the substituent of the alkyl group which is represented by $R^1$ in the general formula [1] and which may have the substituent.

The alkyl group which is mentioned as the substituent and which has 1 to 12 carbon atoms may be any one of straight-chain, branched, and cyclic alkyl groups, and the alkyl group includes one having usually 1 to 12, preferably 1 to 6, and more preferably 1 to 3 carbon atoms. Concrete examples include the same alkyl group as the exemplifications of the alkyl group having 1 to 12 carbon atoms of the alkyl group which is represented by $R^1$ in the general formula [1] and which may have the substituent.

Regarding the method for producing the compound represented by the general formula [1], for example, in an appropriate solvent, the sulfonic acid represented by the general formula [15], an organic base in an amount 1 to 4 times relative to the sulfonic acid concerned, and the compound represented by the general formula [16] in an amount 0.2 to 0.5 times relative to the sulfonic acid concerned on a mol basis are added at 0° C. to 150° C. and, thereafter, a reaction is effected under agitation for 0.5 to 12 hours, so that the desired disulfonic acid ester represented by the general formula [1] is obtained.

Alternatively, the compound represented by the general formula [16] may be reacted with the salt formed from the sulfonic acid represented by the general formula [15] and the organic base concerned, where the salt is prepared by mixing the sulfonic acid represented by the general formula [15] and the organic base in an appropriate solvent in advance, removing the solvent through, if necessary, condensation or the like, and thereafter, precipitating a salt by, if necessary, adding an appropriate poor solvent, followed by isolating the salt through filtration.

As for the reaction solvent used here, a nonaqueous solvent is preferable. Concrete examples include aliphatic hydrocarbons such as hexane, heptane, octane, isooctane, nonane, decane, undecane, dodecane, tridecane, tetradecane, pentadecane, hexadecane, heptadecane, octadecane, cyclohexane, methylcyclohexane, and ethylcyclohexane, or mixtures thereof (for example, paraffin, mineral spirit, and the like); halogenated hydrocarbons such as methylene chloride, methylene bromide, 1,2-dichloroethane, and chloroform; aromatic hydrocarbons such as benzene, toluene, and xylene; carbonates such as dimethyl carbonate, diethyl carbonate, ethylene carbonate, and propylene carbonate; esters such as methyl acetate, ethyl acetate, and butyl acetate; ketones such as acetone and methyl ethyl ketone; ethers such as diethyl ether, isopropyl ether, cyclopentyl methyl ether, tetrahydrofuran, and dioxane; acetonitrile, dimethylformamide, dimethylacetamide, and dimethyl sulfoxide. They may be used alone or at least two types may be used in combination appropriately.

In the case where a mixed solvent is used as the reaction solvent, examples of preferable combinations include a combination of acetonitrile and cyclohexane and a combination of acetonitrile and toluene.

The reaction temperature is usually 0° C. to 150° C., and preferably 20° C. to 100° C.

The reaction time is usually 0.5 to 24 hours, and preferably 0.5 to 12 hours.

Meanwhile, as for the poor solvent used for precipitating in advance the salt formed from the sulfonic acid represented by the general formula [15] and the organic base, any solvent may be employed insofar as the solvent reduces the solubility of the salt concerned, that is, the solvent precipitates the salt concerned. Concrete examples include aliphatic hydrocarbons such as hexane, heptane, octane, isooctane, nonane, decane, undecane, dodecane, tridecane, tetradecane, pentadecane, hexadecane, heptadecane, octadecane, cyclohexane, methylcyclohexane, and ethylcyclohexane, or mixtures thereof (for example, paraffin, mineral spirit, and the like); halogenated hydrocarbons such as methylene chloride, methylene bromide, 1,2-dichloroethane, and chloroform; aromatic hydrocarbons such as benzene, toluene, and xylene; carbonates such as dimethyl carbonate, diethyl carbonate, ethylene carbonate, and propylene carbonate; esters such as methyl acetate, ethyl acetate, and butyl acetate; ketones such as acetone and methyl ethyl ketone; ethers such as diethyl ether, isopropyl ether, cyclopentyl methyl ether, tetrahydrofuran, and dioxane; alcohols such as methanol, ethanol, n-propanol, and isopropanol; and acetonitrile. They may be used alone or at least two types may be used in combination appropriately.

An aftertreatment after the reaction may be performed on the basis of the aftertreatment method usually employed in this field.

As the tertiary amine represented by the general formula [2], commercially available tertiary amine may be used, or the tertiary amine synthesized on the basis of a known method appropriately may be used.

According to the producing method of the present invention, the sulfonic acid salt of the bis-quaternary ammonium salt can be synthesized in one step. Therefore, the bis-quaternary ammonium salt can be produced efficiently in one step, wherein a complicated salt exchange step and a refining step, which are necessary in the conventional step by way of a halide salt, can be omitted and, in addition, problems, e.g., corrosion of equipment, containers, and the like, due to a halogen atom do not occur.

Furthermore, in particular, regarding synthesis of methylene bis-quaternary ammonium salt, in which the alkylene chain of a cross-linking section of a methylene bispyridinium salt or the like is a methylene group (that is, T in the general formula [1] is a methylene group), a low yield is a problem of the conventional method. However, according to the method of the present invention, these methylene bis-quaternary ammonium salts can be produced industrially at a high yield.

The present invention will be further concretely described below with reference to examples and comparative examples. However, the present invention is not limited to them.

EXAMPLES

Synthesis Example 1

Synthesis of methylene bis(methanesulfonate)

In dimethyl carbonate (10 mL), methylene bis(chlorosulfate) [ClSO$_2$OCH$_2$OSO$_2$Cl] (1.5 g, 6.1 mmol) synthesized on the basis of the method described in U.S. Pat. No. 4,649,209 was reacted with methanesulfonic acid pyridinium salt (2.1 g, 12.0 mmol) under agitation at 55° C. for 3 hours. After the reaction was completed, precipitated chlorosulfonic acid pyridinium salt was separated through filtration, and concentration was performed under reduced pressure, so as to obtain a light brown solid. An adsorption treatment with activated carbon was performed and, thereafter, refining was performed through recrystallization, so as to obtain a desired product, methylene bis(methanesulfonate), at a yield of 48% (0.6 g, 2.9 mmol). The measurement result of $^1$H NMR is as described below.

$^1$H NMR (CD$_3$CN); δ=5.80 (s, 2H), 3.19 (s, 6H)

Synthesis Example 2

Synthesis of methylene bis(trifluoromethanesulfonate)

In n-hexane (10 mL), diiodomethane (1.0 g, 3.7 mmol) was reacted with silver trifluoromethanesulfonate (2.0 g, 7.8 mmol) under heating and reflux for 4 hours. After the reaction was completed, precipitated silver iodide was separated through filtration, and concentration was performed under reduced pressure, so as to obtain a light brown oil. An adsorption treatment with activated carbon was performed. Thereafter, the activated carbon was separated through filtration, and concentration was performed under reduced pressure, so as to obtain a desired product, methylene bis(trifluoromethanesulfonate), at a yield of 76% (0.9 g, 2.9 mmol). The measurement result of $^1$H NMR is as described below.

$^1$H NMR (CDCl$_3$); δ=6.06 (s, 2H)

Synthesis Example 3

Methylene bis(ethanesulfonate)

The same treatment as in Synthesis example 1 was performed except that ethanesulfonic acid pyridinium salt (2.3 g, 12.0 mmol) was used instead of methanesulfonic acid pyridinium salt (2.1 g, 12.0 mmol) in Synthesis example 1, so as to obtain methylene bis(ethanesulfonate) at a yield of 41% (0.6 g, 2.5 mmol). The measurement result of $^1$H NMR is as described below.

$^1$H NMR (CDCl$_3$); δ=5.82 (s, 2H), 3.31-3.26 (q, 4H), 1.50-1.46 (t, 6H)

Synthesis Example 4

Methylene bis(octanesulfonate)

The same treatment as in Synthesis example 1 was performed except that octanesulfonic acid pyridinium salt (3.6 g, 12.0 mmol) was used instead of methanesulfonic acid pyridinium salt (2.1 g, 12.0 mmol) in Synthesis example 1, so as to obtain methylene bis(octanesulfonate) at a yield of 35% (0.98 g, 2.1 mmol). The measurement result of $^1$H NMR is as described below.

$^1$H NMR (CDCl$_3$); δ=5.81 (s, 2H), 3.25-3.21 (m, 4H), 1.93-1.85 (m, 4H), 1.46-1.41 (m, 4H), 1.32-1.28 (m, 16H), 0.90-0.87 (t, 6H)

Synthesis Example 5

Methylene bis(vinylsulfonate)

The same treatment as in Synthesis example 1 was performed except that vinylsulfonic acid pyridinium salt (2.2 g, 12.0 mmol) was used instead of methanesulfonic acid pyridinium salt (2.1 g, 12.0 mmol) in Synthesis example 1, so as to obtain methylene bis(vinylsulfonate) at a yield of 61% (0.8 g, 3.7 mmol). The measurement result of $^1$H NMR is as described below.

$^1$H NMR (CD$_3$CN); δ=6.77-6.72 (q, 2H), 6.47-6.43 (d, 2H), 6.29-6.27 (d, 2H), 5.73 (s, 2H)

Synthesis Example 6

Methylene bis(2-benzoyloxyethanesulfonate)

The same treatment as in Synthesis example 1 was performed except that 2-benzoyloxyethanesulfonic acid pyridinium salt (3.7 g, 12.0 mmol) was used instead of methanesulfonic acid pyridinium salt (2.1 g, 12.0 mmol) in Synthesis example 1, so as to obtain methylene bis(2-benzoyloxyethanesulfonate) at a yield of 44% (1.2 g, 2.6 mmol). The measurement result of $^1$H NMR is as described below.

$^1$H NMR (CD$_3$CN); δ=8.04-8.00 (m, 4H), 7.64-7.61 (m, 2H), 7.53-7.47 (m, 4H), 5.88-5.85 (d, 2H), 4.71-4.67 (m, 4H), 3.82-3.71 (m, 4H)

Synthesis Example 7

Methylene bis(benzylsulfonate)

The same treatment as in Synthesis example 1 was performed except that benzylsulfonic acid pyridinium salt (3.0 g, 12.0 mmol) was used instead of methanesulfonic acid pyridinium salt (2.1 g, 12.0 mmol) in Synthesis example 1, so as to obtain methylene bis(benzylsulfonate) at a yield of 31% (0.7 g, 1.9 mmol). The measurement result of $^1$H NMR is as described below.

$^1$H NMR (CD$_3$CN); δ=7.43 (s, 10H), 5.58 (s, 2H), 4.56 (s, 4H)

Synthesis Example 8

Methylene bis(benzenesulfonate)

The same treatment as in Synthesis example 1 was performed except that benzenesulfonic acid pyridinium salt (2.8 g, 12.0 mmol) was used instead of methanesulfonic acid pyridinium salt (2.1 g, 12.0 mmol) in Synthesis example 1, so as to obtain methylene bis(benzenesulfonate) at a yield of 58% (1.2 g, 3.5 mmol). The measurement result of $^1$H NMR is as described below.

$^1$H NMR (CD$_3$CN); δ=7.71-7.69 (m, 6H), 5.58 (s, 2H), 4.56 (s, 4H)

Synthesis Example 9

Methylene bis(4-methylbenzenesulfonate)

The same treatment as in Synthesis example 1 was performed except that 4-methylbenzenesulfonic acid pyridinium salt (3.0 g, 12.0 mmol) was used instead of methanesulfonic acid pyridinium salt (2.1 g, 12.0 mmol) in Synthesis example 1, so as to obtain methylene bis(4-methylbenzenesulfonate) at a yield of 53% (1.2 g, 3.2 mmol). The measurement result of $^1$H NMR is as described below.

$^1$H NMR (CDCl$_3$); δ=7.61-7.58 (d, 4H), 7.26-7.24 (d, 4H), 5.81 (s, 2H), 2.45 (s, 6H)

Synthesis Example 10

Methylene bis(2-naphthalenesulfonate)

The same treatment as in Synthesis example 1 was performed except that 2-naphthalenesulfonic acid pyridinium salt (3.5 g, 12.0 mmol) was used instead of methanesulfonic acid pyridinium salt (2.1 g, 12.0 mmol) in Synthesis example 1, so as to obtain methylene bis(2-naphthalenesulfonate) at a yield of 60% (1.6 g, 3.7 mmol). The measurement result of $^1$H NMR is as described below.

$^1$H NMR (CD$_3$CN); δ=8.25 (s, 2H), 7.87-7.85 (m, 4H), 7.47-7.62 (m, 6H), 7.49-7.47 (d, 2H), 5.95 (s, 2H)

Synthesis Example 11

Methylene bis(1-naphthalenesulfonate)

The same treatment as in Synthesis example 1 was performed except that 1-naphthalenesulfonic acid pyridinium salt (3.4 g, 12.0 mmol) was used instead of methanesulfonic acid pyridinium salt (2.1 g, 12.0 mmol) in Synthesis example 1, so as to obtain methylene bis(1-naphthalenesulfonate) at a yield of 46% (1.2 g, 2.8 mmol). The measurement result of $^1$H NMR is as described below.

$^1$H NMR (CD$_3$CN); δ=8.12-8.10 (m, 4H), 8.03-7.95 (m, 4H), 7.64-7.56 (m, 4H), 7.49-7.41 (t, 2H), 5.83 (s, 2H)

Synthesis Example 12

1,2-bis(methanesulfonyloxy)ethane

Potassium carbonate (6.7 g, 48.5 mmol) and diisopropylethylamine (0.3 g, 2.3 mmol) were suspended in dichloromethane-toluene (1/1, 10 mL), and ethylene glycol (1.5 g, 23.3 mmol) and methanesulfonyl chloride (5.5 g, 48.0 mmol) were dropped at the same time in an ice bath. A reaction was effected at room temperature for 3 hours and, thereafter, the reaction was terminated by addition to ice water. An organic layer separated through liquid separation was concentrated, so as to obtain the desired product, 1,2-bis(methanesulfonyloxy)ethane, at a yield of 36% (1.8 g, 8.4 mmol). The measurement result of $^1$H NMR is as described below.

$^1$H NMR (CD$_3$CN); δ=4.42 (s, 4H), 3.07 (s, 6H)

Synthesis Example 13

1,4-bis(methanesulfonyloxy)butane

The same treatment as in Synthesis example 12 was performed except that 1,4-butanediol (2.1 g, 23.3 mmol) was used instead of ethylene glycol (1.5 g, 23.3 mmol) in Synthesis example 12, so as to obtain 1,4-bis(methanesulfonyloxy)butane at a yield of 21% (1.2 g, 4.9 mmol). The measurement result of $^1$H NMR is as described below.

$^1$H NMR (CD$_3$CN); δ=4.22 (s, 4H), 3.00 (s, 6H), 1.82 (m, 4H)

Synthesis Example 14

Synthesis of methylene bis(2,4,6-trimethylbenzenesulfonate)

The same treatment as in Synthesis example 8 was performed except that mesitylenesulfonic acid pyridinium salt (151 g, 0.540 mol) was used instead of benzenesulfonic acid pyridinium salt (2.8 g, 12.0 mmol) in Synthesis example 8, so as to obtain methylene bis(2,4,6-trimethylbenzenesulfonate) at a yield of 11% (24.3 g, 0.059 mmol). The measurement result of $^1$H NMR is as described below.

$^1$H NMR (DMSO); δ=7.02 (s, 4H), 5.89 (s, 2H), 2.35 (s, 12H), 2.29 (s, 6H)

Synthesis Example 15

Synthesis of methylene bis(4-methoxybenzenesulfonate)

In dimethyl carbonate (30 mL), methylene bis(chlorosulfate) [ClSO$_2$OCH$_2$OSO$_2$Cl] (4.5 g, 13 mmol) was reacted with 4-methoxybenzenesulfonic acid pyridinium salt (7 g, 26 mmol) under agitation at 55° C. for 2 hours. After the reaction was completed, precipitated chlorosulfonic acid pyridinium salt was separated through filtration. Washing with water was performed and, subsequently, concentration was performed under reduced pressure, so as to obtain a pale red transparent oil. Refining was performed through recrystallization, so as to obtain a desired product, methylene bis(4-methoxybenzenesulfonate), at a yield of 32% (1.65 g, 4.2 mmol). The measurement result of $^1$H NMR is as described below.

$^1$H NMR (CDCl$_3$); δ=7.62 (d, 4H), 6.88 (d, 4H), 5.81 (s, 2H), 3.88 (s, 6H)

Synthesis Example 16

Synthesis of methylene bis(4-phenylbenzenesulfonate)

The same treatment as in Synthesis example 8 was performed except that 4-phenylbenzenesulfonic acid pyridinium salt (3.8 g, 12.0 mmol) was used instead of benzenesulfonic acid pyridinium salt (2.8 g, 12.0 mmol) in Synthesis example 8, so as to obtain methylene bis(4-phenylbenzenesulfonate) at a yield of 65% (1.9 g, 3.9 mmol). The measurement result of $^1$H NMR is as described below.

$^1$H NMR (DMSO); δ=7.85-7.80 (m, 8H), 7.68-7.65 (m, 4H), 7.52-7.47 (m, 6H), 6.08 (s, 2H)

Synthesis Example 17

Synthesis of methylene bis(n-butanesulfonate)

The same treatment as in Synthesis example 1 was performed except that n-butanesulfonic acid pyridinium salt (2.6 g, 12.0 mmol) was used instead of methanesulfonic acid pyridinium salt (2.1 g, 12.0 mmol) in Synthesis example 1, so as to obtain methylene bis(n-butanesulfonate) at a yield of 55% (1.0 g, 3.3 mmol). The measurement result of $^1$H NMR is as described below.

$^1$H NMR (DMSO); δ=5.86 (s, 2H), 3.44-3.49 (m, 4H), 1.68-1.73 (m, 4H), 1.37-1.44 (m, 4H), 0.87-0.92 (t, 6H)

Synthesis Example 18.

Synthesis of methylene bis(allylsulfonate)

The same treatment as in Synthesis example 1 was performed except that allylsulfonic acid pyridinium salt (2.4 g, 12.0 mmol) was used instead of methanesulfonic acid pyridinium salt (2.1 g, 12.0 mmol) in Synthesis example 1, so as to obtain methylene bis(allylsulfonate) at a yield of 43% (0.7 g, 2.6 mmol). The measurement result of $^1$H NMR is as described below.

$^1$H NMR (CD$_3$CN); δ=5.93-5.82 (m, 2H), 5.76 (s, 2H), 5.55-5.49 (m, 4H), 4.06-4.04 (d, 4H)

Synthesis Example 19.

Synthesis of methylene bis(2-methylallylsulfonate)

The same treatment as in Synthesis example 1 was performed except that 2-methylallylsulfonic acid pyridinium salt (2.6 g, 12.0 mmol) was used instead of methanesulfonic acid pyridinium salt (2.1 g, 12.0 mmol) in Synthesis example 1, so as to obtain methylene bis(2-methylallylsulfonate) at a yield of 35% (0.6 g, 2.1 mmol). The measurement result of $^1$H NMR is as described below.

$^1$H NMR (CD$_3$CN); δ=5.78 (s, 2H), 5.26-5.20 (d, 4H), 4.04 (s, 4H), 1.93 (s, 6H)

Synthesis Example 20

Synthesis of methylene bis(cinnamylsulfonate)

The same treatment as in Synthesis example 1 was performed except that cinnamylsulfonic acid pyridinium salt (3.3 g, 12.0 mmol) was used instead of methanesulfonic acid pyridinium salt (2.1 g, 12.0 mmol) in Synthesis example 1, so as to obtain methylene bis(cinnamylsulfonate) at a yield of 40% (1.0 g, 2.4 mmol). The measurement result of $^1$H NMR is as described below.

$^1$H NMR (DMSO-d$_6$); δ=7.48 (d, 4H), 7.38-7.30 (m, 6H), 6.83 (d, 2H), 6.29-6.22 (m, 2H), 5.95 (s, 2H), 4.47 (d, 4H)

Synthesis example 21

Synthesis of methylene bis(2-thienylsulfonate)

The same treatment as in Synthesis example 2 was performed except that silver 2-thienylsulfonate acid (2.1 g, 7.8 mmol) was used instead of silver trifluoromethanesulfonate (2.0 g, 7.8 mmol) in Synthesis example 2, so as to obtain methylene bis(2-thienylsulfonate) at a yield of 52% (0.7 g, 2.0 mmol). The measurement result of $^1$H NMR is as described below.

$^1$H NMR (DMSO); δ=8.19-8.21 (m, 2H), 7.81-7.83 (m, 2H), 7.27-7.30 (m, 2H), 6.00 (s, 2H)

Example 1

Methylene bis(4-chlorobenzenesulfonate)

The same treatment as in Synthesis example 1 was performed except that 4-chlorobenzenesulfonic acid pyridinium salt (3.3 g, 12.0 mmol) was used instead of methanesulfonic acid pyridinium salt (2.1 g, 12.0 mmol) in Synthesis example 1, so as to obtain methylene bis(4-chlorobenzenesulfonate) at a yield of 57% (1.3 g, 3.3 mmol). The measurement result of $^1$H NMR is as described below.

$^1$H NMR (CD$_3$CN); δ=7.68-7.60 (d, 4H), 7.53-7.48 (d, 4H), 5.88 (s, 2H)

Example 2

Methylene bis(2,5-dichlorobenzenesulfonate)

The same treatment as in Synthesis example 1 was performed except that 2,5-dichlorobenzenesulfonic acid pyridinium salt (3.0 g, 12.0 mmol) was used instead of methanesulfonic acid pyridinium salt (2.1 g, 12.0 mmol) in Synthesis example 1, so as to obtain methylene bis(2,5-dichlorobenzenesulfonate) at a yield of 58% (1.6 g, 3.5 mmol). The measurement result of $^1$H NMR is as described below.

$^1$H NMR (CDCl$_3$); δ=7.97-7.96 (d, 2H), 7.56-7.53 (dd, 2H), 7.48-7.46 (d, 2H), 6.00 (s, 2H)

Example 3

Methylene bis(4-fluorobenzenesulfonate)

The same treatment as in Synthesis example 2 was performed except that silver 4-fluorobenzenesulfonate (2.2 g, 7.8 mmol) was used instead of silver trifluoromethanesulfonate (2.0 g, 7.8 mmol) in Synthesis example 2, so as to obtain methylene bis(4-fluorobenzenesulfonate) at a yield of 34% (0.5 g, 1.3 mmol). The measurement result of $^1$H NMR is as described below.

$^1$H NMR (CD$_3$CN); δ=7.79-7.76 (d, 4H), 7.29-7.24 (d, 4H), 5.85 (s, 2H)

Example 4

Methylene bis(2,4-difluorobenzenesulfonate)

The same treatment as in Synthesis example 2 was performed except that silver 2,4-difluorobenzenesulfonate (2.3 g, 7.8 mmol) was used instead of silver trifluoromethanesulfonate (2.0 g, 7.8 mmol) in Synthesis example 2, so as to obtain methylene bis(2,4-difluorobenzenesulfonate) at a yield of 78% (1.2 g, 3.0 mmol). The measurement result of $^1$H NMR is as described below.

$^1$H NMR (CDCl$_3$); δ=7.89-7.84 (m, 2H), 7.05-6.95 (m, 4H), 5.96 (s, 2H)

Example 5

Methylene bis(pentafluorobenzenesulfonate)

The same treatment as in Synthesis example 2 was performed except that silver pentafluorobenzenesulfonate (2.7 g, 7.8 mmol) was used instead of silver trifluoromethanesulfonate (2.0 g, 7.8 mmol) in Synthesis example 2, so as to obtain methylene bis(pentafluorobenzenesulfonate) at a yield of 85% (1.7 g, 3.3 mmol). The measurement result of $^1$H NMR is as described below.

$^1$H NMR (CDCl$_3$); δ=6.08 (s, 2H)

Example 6

Methylene bis(3-chloro-4-fluorobenzenesulfonate)

The same treatment as in Synthesis example 2 was performed except that silver 3-chloro-4-fluorobenzenesulfonate (2.4 g, 7.8 mmol) was used instead of silver trifluoromethanesulfonate (2.0 g, 7.8 mmol) in Synthesis example 2, so as to obtain methylene bis(3-chloro-4-fluorobenzenesulfonate) at a yield of 64% (1.1 g, 2.5 mmol). The measurement result of $^1$H NMR is as described below.

$^1$H NMR (CDCl$_3$); δ=5.90 (s, 2H), 7.28 (dd, 2H), 7.68-7.72 (m, 2H), 7.81 (dd, 2H)

Example 7

Methylene bis(4-trifluoromethylbenzenesulfonate)

The same treatment as in Synthesis example 2 was performed except that silver 4-trifluoromethylbenzenesulfonate (2.6 g, 7.8 mmol) was used instead of silver trifluoromethanesulfonate (2.0 g, 7.8 mmol) in Synthesis example 2, so as to obtain methylene bis(4-trifluoromethylbenzenesulfonate) at a yield of 55% (1.0 g, 2.1 mmol). The measurement result of $^1$H NMR is as described below.

$^1$H NMR (CD$_3$CN); δ=7.91-7.89 (d, 4H), 7.83-7.81 (d, 4H), 5.94 (s, 2H)

Example 8

Methylene bis(3-trifluoromethylbenzenesulfonate)

The same treatment as in Synthesis example 2 was performed except that silver 3-(trifluoromethyl)benzenesulfonate (2.6 g, 7.8 mmol) was used instead of silver trifluoromethanesulfonate (2.0 g, 7.8 mmol) in Synthesis example 2, so as to obtain methylene bis(3-(trifluoromethyl)benzenesulfonate) at a yield of 45% (0.81 g, 1.8 mmol). The measurement result of $^1$H NMR is as described below.

$^1$H NMR (CDCl$_3$); δ=5.94 (s, 2H), 7.65 (t, 2H), 7.90 (d, 2H), 7.96 (d, 2H), 8.02 (s, 2H)

Example 9

Methylene bis(2-trifluoromethylbenzenesulfonate)

The same treatment as in Synthesis example 2 was performed except that silver 2-(trifluoromethyl)benzenesulfonate (2.6 g, 7.8 mmol) was used instead of silver trifluoromethanesulfonate (2.0 g, 7.8 mmol) in Synthesis example 2, so as to obtain methylene bis(2-(trifluoromethyl)benzenesulfonate) at a yield of 39% (0.71 g, 1.5 mmol). The measurement result of $^1$H NMR is as described below.

¹H NMR (CDCl₃); δ=5.94 (s, 2H), 7.71-7.85 (m, 6H), 8.15 (d, 2H)

Example 10

Methylene bis(pyridinium methanesulfonate)

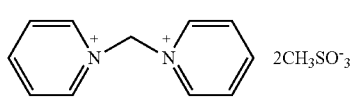

Methylene bis(methanesulfonate) (1.0 g, 4.9 mmol) obtained in Synthesis example 1 and pyridine (0.78 g, 9.8 mmol) were mixed and agitation was performed at 80° C. for 2 hours. After the reaction, desired methylene bis(pyridinium methanesulfonate) was obtained at a yield of 82% (1.5 g, 4.0 mmol) through dissolution into methanol and addition of acetone to cause crystallization. The measurement result of ¹H NMR is as described below.

¹H NMR (CD₃OD); δ=9.44-9.43 (d, 4H), 8.86-8.81 (t, 2H), 8.34-8.30 (m, 4H), 7.39 (s, 2H)

Example 11

Methylene bis(pyridinium trifluoromethanesulfonate)

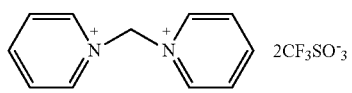

The same treatment as in Example 10 was performed except that methylene bis(trifluoromethanesulfonate) (1.5 g, 4.9 mmol) obtained in Synthesis example 2 was used instead of methylene bis(methanesulfonate) (1.0 g, 4.9 mmol) in Example 10, so as to obtain methylene bis(pyridinium trifluoromethanesulfonate) at a yield of 79% (1.8 g, 3.9 mmol). The measurement result of ¹H NMR is as described below.

¹H NMR (acetone-d₆); δ=9.78-9.76 (d, 4H), 9.01-8.97 (t, 2H), 8.50-8.46 (m, 4H), 7.79 (s, 2H)

Example 12

Methylene bis(pyridinium ethanesulfonate)

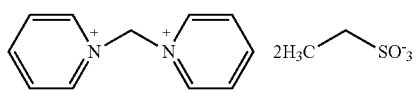

The same treatment as in Example 10 was performed except that methylene bis(ethanesulfonate) (1.1 g, 4.9 mmol) obtained in Synthesis example 3 was used instead of methylene bis(methanesulfonate) (1.0 g, 4.9 mmol) in Example 10, so as to obtain methylene bis(pyridinium ethanesulfonate) at a yield of 73% (1.4 g, 3.6 mmol). The measurement result of ¹H NMR is as described below.

¹H NMR (CD₃OD); δ=9.44-9.42 (d, 4H), 8.86-8.82 (t, 2H), 8.34-8.31 (m, 4H), 7.39 (s, 2H)

Example 13

Methylene bis(pyridinium benzylsulfonate)

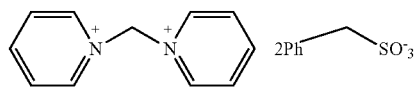

The same treatment as in Example 10 was performed except that methylene bis(benzylsulfonate) (1.4 g, 4.9 mmol) obtained in Synthesis example 7 was used instead of methylene bis(methanesulfonate) (1.0 g, 4.9 mmol) in Example 10, so as to obtain methylene bis(pyridinium benzylsulfonate) at a yield of 68% (1.5 g, 3.3 mmol). The measurement result of ¹H NMR is as described below.

¹H NMR (CD₃OD); δ=9.29-9.28 (d, 4H), 8.78-8.74 (t, 2H), 8.21-8.18 (t, 4H), 7.41-7.40 (d, 4H), 7.30-7.22 (m, 8H), 4.05 (s, 4H)

Example 14

Methylene bis(pyridinium 4-methylbenzenesulfonate)

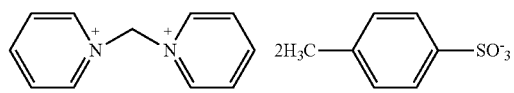

The same treatment as in Example 10 was performed except that methylene bis(4-methylbenzenesulfonate) (1.8 g, 4.9 mmol) obtained in Synthesis example 9 was used instead of methylene bis(methanesulfonate) (1.0 g, 4.9 mmol) in Example 10, so as to obtain methylene bis(pyridinium 4-methylbenzenesulfonate) at a yield of 67% (1.7 g, 3.3 mmol). The measurement result of ¹H NMR is as described below.

¹H NMR (CD₃OD); δ=9.41-9.40 (d, 4H), 8.81-8.79 (t, 2H), 8.28-8.26 (t, 4H), 7.68-7.66 (d, 4H), 7.38 (s, 2H), 7.24-7.22 (d, 4H), 2.36 (s, 6H)

Example 15

Methylene bis(pyridinium 2-naphthalenesulfonate)

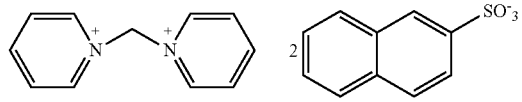

The same treatment as in Example 10 was performed except that methylene bis(2-naphthalenesulfonate) (2.1 g, 4.9 mmol) obtained in Synthesis example 10 was used instead of methylene bis(methanesulfonate) (1.0 g, 4.9 mmol) in Example 10, so as to obtain methylene bis(pyridinium 2-naphthalenesulfonate) at a yield of 72% (2.0 g, 3.4 mmol). The measurement result of ¹H NMR is as described below.

$^1$H NMR (acetone-d$_6$); δ=9.79-9.78 (d, 4H), 8.89-8.86 (t, 2H), 8.40-8.36 (t, 4H), 8.33 (s, 2H), 7.98-7.91 (m, 8H), 7.79 (s, 2H), 7.57-7.55 (m, 4H)

Example 16

Ethylene Bis(Pyridinium Methanesulfonate)

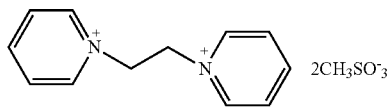

The same treatment as in Example 10 was performed except that 1,2-bis(methanesulfonyloxy)ethane (1.1 g, 4.9 mmol) obtained in Synthesis example 12 was used instead of methylene bis(methanesulfonate) (1.0 g, 4.9 mmol) in Example 10, so as to obtain ethylene bis(pyridinium methanesulfonate) at a yield of 69% (1.3 g, 3.4 mmol). The measurement result of $^1$H NMR is as described below.

$^1$H NMR (CD$_3$OD); δ=9.02-9.01 (d, 4H), 8.67-8.65 (t, 2H), 8.18-8.17 (t, 4h), 5.01 (s, 4H), 2.69 (s, 6H)

Example 17

Tetramethylene bis(pyridinium methanesulfonate)

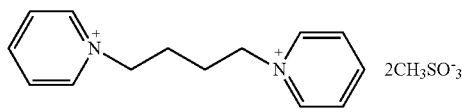

The same treatment as in Example 10 was performed except that 1,4-bis(methanesulfonyloxy)butane (1.2 g, 4.9 mmol) obtained in Synthesis example 13 was used instead of methylene bis(methanesulfonate) (1.0 g, 4.9 mmol) in Example 10, so as to obtain tetramethylene bis(pyridinium methanesulfonate) at a yield of 68% (1.3 g, 3.3 mmol). The measurement result of $^1$H NMR is as described below.

$^1$H NMR (CD$_3$OD); δ=9.02-9.01 (d, 4H), 8.60-8.59 (t, 2H), 8.13-8.12 (t, 4H), 4.72 (s, 4H), 2.70 (s, 6H), 2.14 (s, 4H)

Example 18

Methylene bis(3-methylpyridinium methanesulfonate)

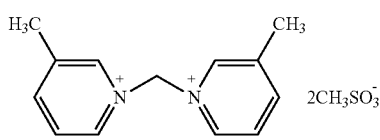

The same treatment as in Example 10 was performed except that 3-methylpyridine (0.91 g, 9.8 mmol) was used instead of pyridine (0.78 g, 9.8 mmol) in Example 10, so as to obtain methylene bis(3-methylpyridinium methanesulfonate) at a yield of 77% (1.5 g, 3.8 mmol). The measurement result of $^1$H NMR is as described below.

$^1$H NMR (CD$_3$OD); δ=9.27 (s, 2H), 9.23-9.22 (m, 2H), 8.67-8.85 (m, 2H), 8.20-8.17 (m, 2H), 2.69 (s, 6H), 2.64 (s, 6H)

Example 19

Methylene bis(3,5-dimethylpyridinium methanesulfonate)

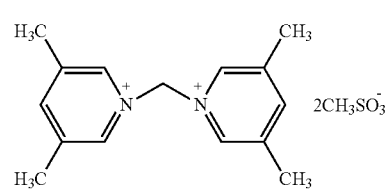

The same treatment as in Example 10 was performed except that 3,5-dimethylpyridine (1.05 g, 9.8 mmol) was used instead of pyridine (0.78 g, 9.8 mmol) in Example 10, so as to obtain methylene bis(3,5-dimethylpyridinium methanesulfonate) at a yield of 85% (1.7 g, 4.2 mmol). The measurement result of $^1$H NMR is as described below.

$^1$H NMR (CD$_3$OD); δ=9.09 (s, 4H), 8.49 (s, 2H), 7.15 (s, 2H), 2.67 (s, 6H)

Example 20

Methylene bis(1-methylimidazolium methanesulfonate)

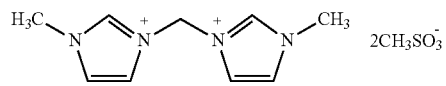

The same treatment as in Example 10 was performed except that 1-methylimidazol (0.81 g, 9.8 mmol) was used instead of pyridine (0.78 g, 9.8 mmol) in Example 10, so as to obtain methylene bis(1-methylimidazolium methanesulfonate) at a yield of 84% (1.5 g, 4.1 mmol). The measurement result of $^1$H NMR is as described below.

$^1$H NMR (CD$_3$OD); δ=9.35 (s, 2H), 7.92 (s, 2H), 7.70 (s, 2H), 6.70 (s, 2H), 3.98 (s, 6H), 2.70 (s, 6H)

Example 21

Methylene bis(1,2-dimethylimidazolium methanesulfonate)

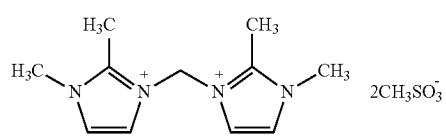

The same treatment as in Example 10 was performed except that 1,2-dimethylimidazol (0.94 g, 9.8 mmol) was used instead of pyridine (0.78 g, 9.8 mmol) in Example 10, so as to obtain methylene bis(1,2-dimethylimidazolium methanesulfonate) at a yield of 88% (1.7 g, 4.3 mmol). The measurement result of $^1$H NMR is as described below.

¹H NMR (CD₃OD); δ=7.73 (s, 2H), 7.62 (s, 2H), 6.61 (s, 2H), 3.87 (s, 6H), 2.79 (s, 6H), 2.66 (s, 6H)

Example 22

Methylene bis(3-methylpyridinium trifluoromethanesulfonate)

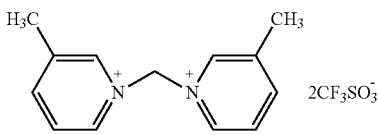

The same treatment as in Example 18 was performed except that methylene bis(trifluoromethanesulfonate) (1.5 g, 4.9 mmol) was used instead of methylene bis(methanesulfonate) (1.0 g, 4.9 mmol) in Example 18, so as to obtain methylene bis(3-methylpyridinium trifluoromethanesulfonate) at a yield of 68% (1.7 g, 3.3 mmol). The measurement result of ¹H NMR is as described below.

¹H NMR (CD₃OD); δ=9.21-9.16 (d, 4H), 8.65 (s, 2H), 8.17 (s, 2H), 7.22 (s, 2H), 2.63 (s, 6H)

Example 23

Methylene bis(tributylammonium trifluoromethanesulfonate)

*Bu=n-butyl group

The same treatment as in Example 10 was performed except that methylene bis(trifluoromethanesulfonate) (1.5 g, 4.9 mmol) was used instead of methylene bis(methanesulfonate) (1.0 g, 4.9 mmol) and tributylamine (1.82 g, 9.8 mmol) was used instead of pyridine (0.78 g, 9.8 mmol) in Example 10, so as to obtain methylene bis(tributylammonium trifluoromethanesulfonate) at a yield of 77% (2.6 g, 3.8 mmol). The measurement result of ¹H NMR is as described below.

¹H NMR (CD₃OD); δ=5.84 (s, 2H), 3.46-3.42 (m, 8H), 3.14-3.10 (m, 4H), 1.74-1.65 (m, 12H), 1.45-1.40 (m, 12H), 1.05-0.99 (m, 18H)

Example 24

Ethylene bis(3-methylpyridinium methanesulfonate)

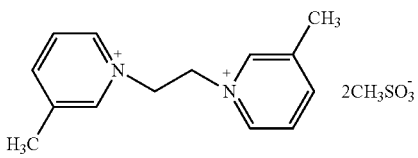

The same treatment as in Example 16 was performed except that 3-methylpyridine (0.91 g, 9.8 mmol) was used instead of pyridine (0.78 g, 9.8 mmol) in Example 16, so as to obtain ethylene bis(3-methylpyridinium methanesulfonate) at a yield of 76% (1.5 g, 3.7 mmol). The measurement result of ¹H NMR is as described below.

¹H NMR (CD₃OD); δ=8.95-8.92 (d, 2H), 8.79-8.75 (d, 2H), 8.54-8.52 (d, 2H), 8.06-8.02 (t, 2H), 5.24 (s, 4H), 2.70 (s, 6H), 2.60 (s, 6H)

Example 25

Tetramethylene bis(3-methylpyridinium methanesulfonate)

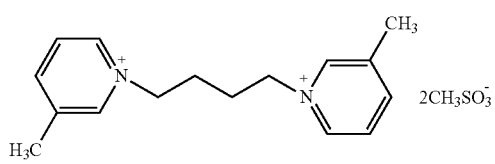

The same treatment as in Example 17 was performed except that 3-methylpyridine (0.91 g, 9.8 mmol) was used instead of pyridine (0.78 g, 9.8 mmol) in Example 17, so as to obtain tetramethylene bis(3-methylpyridinium methanesulfonate) at a yield of 69% (1.5 g, 3.4 mmol). The measurement result of ¹H NMR is as described below.

¹H NMR (CD₃OD); δ=8.89 (s, 2H), 8.83-8.81 (d, 2H), 8.44-8.42 (d, 2H), 8.01-7.98 (t, 2H), 4.66 (s, 4H), 2.70 (s, 6H), 2.58 (s, 6H), 2.12 (s, 4H)

Example 26

Tetramethylene bis(3,5-dimethylpyridinium methanesulfonate)

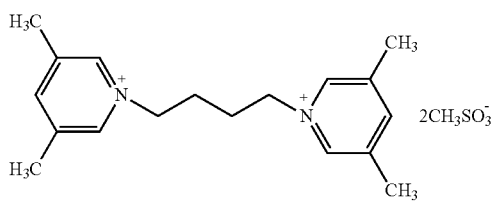

The same treatment as in Example 17 was performed except that 3,5-dimethylpyridine (1.05 g, 9.8 mmol) was used instead of pyridine (0.78 g, 9.8 mmol) in Example 17, so as to obtain tetramethylene bis(3,5-dimethylpyridinium methanesulfonate) at a yield of 67% (1.5 g, 3.3 mmol). The measurement result of ¹H NMR is as described below.

¹H NMR (CD₃OD); δ=8.69 (s, 4H), 8.26 (s, 2H), 4.60 (m, 4H), 2.69 (s, 6H), 2.53 (s, 12H), 2.10-2.09 (m, 4H)

Example 27

Tetramethylene bis(1-methylimidazolium methanesulfonate)

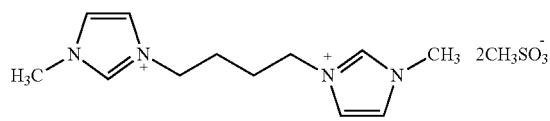

The same treatment as in Example 17 was performed except that 1-methylimidazol (0.80 g, 9.8 mmol) was used instead of pyridine (0.78 g, 9.8 mmol) in Example 17, so as to obtain tetramethylene bis(1-methylimidazolium methanesulfonate) at a yield of 80% (1.6 g, 3.9 mmol). The measurement result of $^1$H NMR is as described below.

$^1$H NMR (CD$_3$OD); δ=8.93 (s, 2H), 7.61 (s, 2H), 7.53 (s, 2H), 4.25 (s, 4H), 3.89 (s, 6H), 2.65 (s, 6H), 1.91-1.89 (t, 4H)

Comparative Example 1

Synthesis of methylene bis(pyridinium bromide) by Conventional Method

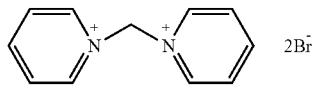

Dibromomethane (0.85 g, 4.9 mmol) and pyridine (0.78 g, 9.8 mmol) were mixed and agitation was performed at 80° C. for 4 hours. After the reaction, desired methylene bis(pyridinium bromide) was obtained at a yield of 29% (0.5 g, 1.4 mmol) through dissolution into methanol and addition of acetone to cause crystallization. The measurement result of $^1$H NMR is as described below.

$^1$H NMR (D$_2$O); δ=9.23-9.21 (d, 4H), 8.74-8.70 (t, 2H), 8.21-8.17 (t, 4H), 7.33 (s, 2H)

As is clear from the results of Example 1 to Example 27 and Comparative example 1, regarding the conventional method, the desired product, bis-quaternary ammonium salt, is obtained at a low yield even when the reaction time is large (Comparative example 1), whereas regarding the method according to the present invention, the bis-quaternary ammonium salt can be obtained at a high yield in spite of a short reaction time.

Experiment Example 1

Cyclic Voltammetry Measurement by Using Compound of Example 1

(1) Preparation of Electrolyte 1

A lithium salt, LiPF$_6$, was dissolved into an equal volume mixed solvent (EC/DEC=1/1) of ethylene carbonate (EC) and diethyl carbonate (DEC) in such a way that 1 mol/L was ensured (Reference electrolyte). The compound of Example 1 was added respectively to the resulting Reference electrolyte in such a way as to become 1 percent by weight relative to the total amount of electrolyte (Electrolyte 1).

(2) Cyclic Voltammetry (Cv) Measurement

Electrolyte 1 was put into a three-electrode beaker cell, in which GCE glassy carbon (0.07 cm$^2$) produced by BAS was used as a working electrode, a Li metal (0.5 cm$^2$) was used as a reference electrode, and a Li metal (3.75 cm$^2$) was used as a counter electrode, and measurement was performed with HZ-3000 produced by HOKUTO DENKO CORPORATION. Sweeping was performed two times over spontaneous potential of 3 V to 0 V at a sweep rate of 5 my/s, so as to form a cyclic voltammogram.

Regarding the electrolyte, a potential, at which a current derived from reductive decomposition of the additive was observed, was determined on the basis of the resulting cyclic voltammogram. The results thereof are shown in Table 1.

Experiment Examples 2 and 9

Each of Electrolytes 2 to 9 was prepared by performing the same operation as in Experiment example 1 except that the compounds of Examples 2 to 9 were used as the additives of the electrolytes instead of the compound of Example 1. Through the use of this, a potential, at which a current derived from reductive decomposition of the additive was observed, was determined on the basis of the CV measurement. The results thereof are also shown in Table 1.

Furthermore, the cyclic voltammogram of Example 7 (the case where the compound of Example 7 was used) is shown in FIG. 1.

Comparative Examples 2 to 6

Electrolytes were prepared by performing the same operation as in Experiment example 1 except that the compounds of Synthesis examples 1 to 3, 9, and 12 were used as the additives of the electrolytes instead of the compound of Example 1. Through the use of this, a potential, at which a current derived from reductive decomposition of the additive was observed, was determined on the basis of the CV measurement. The results thereof are also shown in Table 1.

TABLE 1

| | Additive | Reductive decomposition potential |
|---|---|---|
| Experiment example 1 | [Example 1] Methylene bis(4-chlorobenzenesulfonate) | 1.6 V |
| Experiment example 2 | [Example 2] Methylene bis(2,5-dichlorobenzenesulfonate) | 1.8 V |
| Experiment example 3 | [Example 3] Methylene bis(4-fluorobenzenesulfonate) | 1.8 V |
| Experiment example 4 | [Example 4] Methylene bis(2,4-difluorobenzenesulfonate) | 1.8 V |
| Experiment example 5 | [Example 5] Methylene bis(pentafluorobenzenesulfonate) | 2.0 V |
| Experiment example 6 | [Example 6] Methylene bis(2-chloro-3-fluorobenzenesulfonate) | 1.8 V |
| Experiment example 7 | [Example 7] Methylene bis(4-trifluoromethylbenzenesulfonate) | 1.8 V |
| Experiment example 8 | [Example 8] Methylene bis(3-(trifluoromethyl)benzenesulfonate) | 1.8 V |
| Experiment example 9 | [Example 9] Methylene bis(2-(trifluoromethyl)benzenesulfonate) | 1.8 V |

TABLE 1-continued

| Additive | | Reductive decomposition potential |
|---|---|---|
| Comparative example 2 | [Synthesis example 1] Methylene bis(methanesulfonate) | 0 V or less |
| Comparative example 3 | [Synthesis example 2] Methylene bis(trifluoromethanesulfonate) | 1.4 V |
| Comparative example 4 | [Synthesis example 3] Methylene bis(benzenesulfonate) | 1.4 V |
| Comparative example 5 | [Synthesis example 9] Methylene bis(4-methylbenzenesulfonate) | 1.4 V |
| Comparative example 6 | [Synthesis example 12] 1,2-bis(methanesulfonyloxy)ethane | 0.4 V |

As is clear from the results of Examples 1 to 9 shown in Table 1, regarding any one of electrolytes containing disulfonic acid esters, which were novel compounds and which were represented by the general formula [1'], as additives, a current derived from reductive decomposition of the additive was observed at a potential nobler than 1.6 V.

In this regard, as for the measurement in the reduction side, the measurement is performed by sweeping from a noble potential toward a base potential and, therefore, a larger numerical value refers to the fact that reductive decomposition proceeds with a smaller amount of charge consumption.

That is, it is made clear that the disulfonic acid ester represented by the general formula [1'] undergoes reductive decomposition with a small amount of charge consumption as compared with comparative compounds (compounds of Synthesis examples 1 to 3, 9, and 12).

Meanwhile, as is clear from the results shown in FIG. 1, in the second sweep, neither reduction peak (1.8 V) of the additive nor reduction peak (0.4 V or less) of the electrolyte was observed, although the two were observed in the first sweep. Therefore, it was found that a passive film (SEI: solid electrolyte interface) was formed through reductive decomposition of the additive (the compound of Example 7) and reduction of the electrolyte was suppressed.

That is, regarding the electrolyte by using the disulfonic acid ester serving as the additive, according to the present invention, the additive undergoes reductive decomposition with a small amount of charge consumption and a passive film (SEI: solid electrolyte interface) is formed on the negative electrode as compared with the electrolyte containing the comparative compound which has a structure analogous to the structure of the above-described ester and which serves as the additive.

As described above, in the case where the electrolyte containing the disulfonic acid ester serving as an additive, according to the present invention, is used for a lithium secondary battery, a stable passive film (SEI: solid electrolyte interface) is generated with a small amount of charge consumption. Consequently, a battery exhibiting excellent cycle characteristics and, in addition, having a small irreversible capacity and a large charge and discharge capacity can be provided.

What is claimed is:

1. A method for producing a bis-quaternary ammonium salt represented by a formula (3), which comprises reacting a disulfonic acid ester represented by a formula (1) with a tertiary amine represented by a formula (2):

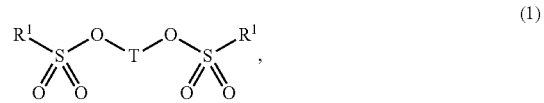

(1)

wherein $R^1$ represents an alkyl group, which may have at least one substituent, a haloalkyl group, a heteroatom-containing alkyl group, which may have at least one substituent, a phenyl group, which may have at least one substituent selected from the group consisting of halogen and a $C_1$-$C_3$ fluoroalkyl group independently, an aralkyl group, which may have at least one substituent, a heterocyclic group, which may have at least one substituent, or an unsaturated hydrocarbon group, and T represents a $C_1$-$C_3$ alkylene chain,

(2)

wherein $R^3$ to $R^5$ represent independently an alkyl group or a heteroatom-containing alkyl group, $R^3$ and $R^4$ or $R^3$ to $R^5$ and nitrogen bonding thereto may form a heterocycle, and

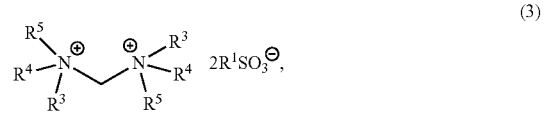

(3)

wherein $R^1$, $R^3$ to $R^5$, and T are the same as the above.

2. The producing method according to claim 1, wherein T is a methylene group.

3. The producing method according to claim 1, wherein the tertiary amine represented by the formula (2) is pyridine, 3-methylpyridine, 3,5-dimethylpyridine, 1-methylimidazole, 1,2-dimethylimidazole, or tributylamine.

4. A disulfonic acid ester represented by a following formula (1'):

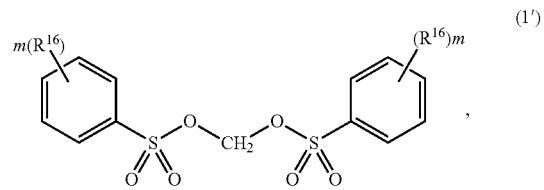

(1')

wherein, two $R^{16}$s represent independently halogen or a $C_1$-$C_3$ fluoroalkyl group, and two ms represent independently an integer from 1 to 5.

5. The producing method according to claim 1, wherein $R^1$ is a methyl group or trifluoromethyl group.

* * * * *